(12) United States Patent
Bernick et al.

(10) Patent No.: US 8,846,648 B2
(45) Date of Patent: *Sep. 30, 2014

(54) NATURAL COMBINATION HORMONE REPLACEMENT FORMULATIONS AND THERAPIES

(71) Applicant: TherapeuticsMD, Inc., Boca Raton, FL (US)

(72) Inventors: Brian A. Bernick, Boca Raton, FL (US); Janice Louise Cacace, Miami, FL (US); Peter H. R. Persicaner, Boca Raton, FL (US); Neda Irani, Palm Beach Garden, FL (US); Julia M. Amadio, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/099,545

(22) Filed: Dec. 6, 2013

(65) Prior Publication Data

US 2014/0088051 A1 Mar. 27, 2014

Related U.S. Application Data

(62) Division of application No. 13/684,002, filed on Nov. 21, 2012, now Pat. No. 8,633,178.

(60) Provisional application No. 61/662,265, filed on Jun. 20, 2012, provisional application No. 61/661,302, filed on Jun. 18, 2012, provisional application No. 61/563,408, filed on Nov. 23, 2011.

(51) Int. Cl.
| | | |
|---|---|---|
| *A01N 45/00* | (2006.01) | |
| *A61K 9/48* | (2006.01) | |
| *A61K 31/565* | (2006.01) | |
| *A61K 9/16* | (2006.01) | |
| *A61K 31/57* | (2006.01) | |

(52) U.S. Cl.
CPC .............. *A61K 31/57* (2013.01); *A61K 9/4858* (2013.01); *A61K 31/565* (2013.01); *A61K 9/16* (2013.01)
USPC .......................................... 514/169; 424/452

(58) Field of Classification Search
USPC ....................................................... 514/169
See application file for complete search history.

(56) References Cited

U.S. PATENT DOCUMENTS

| | | | |
|---|---|---|---|
| 1,967,351 A | 7/1934 | Doisy | |
| 2,379,832 A | 7/1945 | Serini et al. | |
| 2,649,399 A | 8/1953 | Grant et al. | |
| 3,198,707 A | 8/1965 | Nomaine et al. | |
| 3,478,070 A | 11/1969 | Smith et al. | |
| 3,526,648 A | 9/1970 | Bertin et al. | |
| 3,710,795 A | 1/1973 | Higuchi et al. | |
| 3,729,560 A | 4/1973 | Hagerman | |
| 3,729,566 A | 4/1973 | Ericsson et al. | |
| 3,755,573 A | 8/1973 | Berman | |
| 3,755,575 A | 8/1973 | Lerner | |
| 3,903,880 A | 9/1975 | Higuchi et al. | |
| 3,916,898 A | 11/1975 | Robinson | |
| 3,916,899 A | 11/1975 | Higuchi et al. | |
| 3,921,636 A | 11/1975 | Zaffaroni | |
| 3,923,997 A | 12/1975 | Meuly | |
| 3,948,254 A | 4/1976 | Zaffaroni | |
| 3,971,367 A | 7/1976 | Zaffaroni | |
| 3,977,404 A | 8/1976 | Theeuwes | |
| 3,993,072 A | 11/1976 | Zaffaroni | |
| 4,008,719 A | 2/1977 | Theeuwes | |
| 4,012,496 A | 3/1977 | Hartmann et al. | |
| 4,014,334 A | 3/1977 | Theeuwes et al. | |
| 4,014,987 A | 3/1977 | Heller et al. | |
| 4,016,251 A | 4/1977 | Higuchi et al. | |
| 4,071,623 A | 1/1978 | Van Der Vies | |
| 4,093,709 A | 6/1978 | Choi | |
| 4,154,820 A | 5/1979 | Simoons | |
| 4,155,991 A | 5/1979 | Schopflin et al. | |
| 4,196,188 A | 4/1980 | Besins | |
| 4,215,691 A | 8/1980 | Wong | |
| 4,237,885 A | 12/1980 | Wong | |
| 4,310,510 A | 1/1982 | Sherman et al. | |
| 4,327,725 A | 5/1982 | Cortese et al. | |
| 4,372,951 A | 2/1983 | Vorys | |
| 4,384,096 A | 5/1983 | Sonnabend | |

(Continued)

FOREIGN PATENT DOCUMENTS

| | | |
|---|---|---|
| CN | 102258455 A | 11/2011 |
| EP | 0275716 A1 | 7/1988 |
| EP | 0622075 A1 | 11/1994 |
| EP | 0785211 A1 | 1/1996 |
| EP | 0811381 A1 | 6/1997 |

(Continued)

OTHER PUBLICATIONS

Chempro, "Fatty Acid Composition of Some Major Oils," available at http://www.chempro.in/fattyacid.htm, webpage captured on May 26, 2010 (2 total pages).*

(Continued)

*Primary Examiner* — Frederick Krass
*Assistant Examiner* — Dennis J Parad
(74) *Attorney, Agent, or Firm* — Kilpatrick Townsend & Stockton LLP; Marian D. Walker

(57) ABSTRACT

Estrogen and progesterone replacement therapies are provided herein. Among others, the following formulations are provided herein: solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; and solubilized estradiol with solubilized progesterone.

20 Claims, 4 Drawing Sheets

(56) References Cited

U.S. PATENT DOCUMENTS

| | | |
|---|---|---|
| 4,393,871 A | 7/1983 | Vorhauer |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A * | 2/1990 | Maxson et al. ............... 514/171 |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley |
| 5,140,021 A | 8/1992 | Maxson et al. |
| 5,211,952 A | 5/1993 | Pike et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmuller et al. |
| 5,516,528 A | 5/1996 | Hughes et al. |
| 5,527,534 A | 6/1996 | Myhling |
| 5,529,782 A | 6/1996 | Staab |
| 5,543,150 A | 8/1996 | Bologna et al. |
| 5,547,948 A | 8/1996 | Barcomb |
| 5,565,199 A | 10/1996 | Page et al. |
| 5,567,831 A | 10/1996 | Li |
| 5,569,652 A | 10/1996 | Beier et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,620,705 A | 4/1997 | Dong et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,656,286 A | 8/1997 | Miranda et al. |
| 5,676,968 A | 10/1997 | Lipp et al. |
| 5,677,292 A | 10/1997 | Li et al. |
| 5,694,947 A | 12/1997 | Lehtinen et al. |
| 5,709,844 A | 1/1998 | Arbeit et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,776,495 A | 7/1998 | Duclos et al. |
| 5,788,980 A | 8/1998 | Nabahi |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,827,200 A | 10/1998 | Caillouette |
| 5,866,603 A | 2/1999 | Li et al. |
| 5,891,868 A | 4/1999 | Cummings et al. |
| 5,898,038 A | 4/1999 | Yallampalli et al. |
| 5,916,176 A | 6/1999 | Caillouette |
| RE36,247 E | 7/1999 | Plunkett et al. |
| 5,922,349 A | 7/1999 | Elliesen et al. |
| 5,928,666 A | 7/1999 | Farinas et al. |
| 5,958,446 A | 9/1999 | Miranda et al. |
| 5,962,445 A | 10/1999 | Stewart |
| 5,972,372 A | 10/1999 | Saleh et al. |
| 5,985,861 A | 11/1999 | Levine et al. |
| 5,993,856 A | 11/1999 | Ragavan et al. |
| 6,001,846 A | 12/1999 | Edwards et al. |
| 6,022,562 A | 2/2000 | Autant et al. |
| 6,024,976 A | 2/2000 | Miranda et al. |
| 6,028,057 A | 2/2000 | Burns |
| 6,039,968 A | 3/2000 | Nabahi |
| 6,056,972 A | 5/2000 | Hermsmeyer |
| 6,060,077 A | 5/2000 | Meignant |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,096,338 A | 8/2000 | Lacy et al. |
| 6,117,446 A | 9/2000 | Place |
| 6,117,450 A | 9/2000 | Dittgen et al. |
| 6,133,251 A | 10/2000 | Dittgen et al. |
| 6,133,320 A | 10/2000 | Yallampalli et al. |
| 6,139,873 A | 10/2000 | Hughes, Jr. et al. |
| 6,153,216 A | 11/2000 | Cordes et al. |
| 6,165,491 A | 12/2000 | Grasset et al. |
| 6,165,975 A | 12/2000 | Adams et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,227,202 B1 | 5/2001 | Matapurkar |
| 6,262,115 B1 | 7/2001 | Guittard et al. |
| 6,277,418 B1 | 8/2001 | Markaverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,306,841 B1 | 10/2001 | Place et al. |
| 6,306,914 B1 | 10/2001 | Ziegler et al. |
| 6,309,669 B1 | 10/2001 | Setterstrom et al. |
| 6,309,848 B1 | 10/2001 | Howett et al. |
| 6,342,491 B1 | 1/2002 | Dey et al. |
| 6,372,209 B1 | 4/2002 | Chrisope |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,423,039 B1 | 7/2002 | Rathbone et al. |
| 6,423,683 B1 | 7/2002 | Heaton et al. |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,526,980 B1 | 3/2003 | Tracy et al. |
| 6,528,094 B1 | 3/2003 | Savoir et al. |
| 6,537,580 B1 | 3/2003 | Savoir et al. |
| 6,544,196 B2 | 4/2003 | Caillouette |
| 6,544,553 B1 | 4/2003 | Hsia et al. |

(56) References Cited

U.S. PATENT DOCUMENTS

| | | |
|---|---|---|
| 6,548,491 B2 | 4/2003 | Tanabe et al. |
| 6,551,611 B2 | 4/2003 | Elliesen et al. |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,610,652 B2 | 8/2003 | Adams et al. |
| 6,610,670 B2 | 8/2003 | Backensfeld et al. |
| 6,638,536 B2 | 10/2003 | Savoir et al. |
| 6,645,528 B1 | 11/2003 | Straub et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,692,763 B1 | 2/2004 | Cummings et al. |
| 6,737,081 B2 | 5/2004 | Savoir et al. |
| 6,740,333 B2 | 5/2004 | Beckett et al. |
| 6,743,815 B2 | 6/2004 | Navaratnam et al. |
| 6,747,018 B2 | 6/2004 | Tanabe et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Huebner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,977,250 B2 | 12/2005 | Rodriguez |
| 6,978,945 B2 | 12/2005 | Wong et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,157 B2 | 4/2006 | Ke et al. |
| RE39,104 E | 5/2006 | Duclos et al. |
| 7,074,779 B2 | 7/2006 | Sue et al. |
| 7,083,590 B1 | 8/2006 | Bunt et al. |
| 7,091,213 B2 | 8/2006 | Metcalf, III et al. |
| 7,101,342 B1 | 9/2006 | Caillouette |
| 7,135,190 B2 | 11/2006 | Piao et al. |
| 7,163,681 B2 | 1/2007 | Giles-Komar et al. |
| 7,163,699 B2 | 1/2007 | Besse |
| 7,179,799 B2 | 2/2007 | Hill et al. |
| 7,196,074 B2 | 3/2007 | Blye et al. |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,534,765 B2 | 5/2009 | Gregg et al. |
| 7,550,142 B2 | 6/2009 | Giles-Komar et al. |
| 7,563,565 B1 | 7/2009 | Matsuo et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,815,949 B2 | 10/2010 | Cohen |
| 7,829,115 B2 | 11/2010 | Besins et al. |
| RE42,012 E | 12/2010 | Deaver et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,879,830 B2 | 2/2011 | Wiley |
| 7,884,093 B2 | 2/2011 | Creasy et al. |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,869 B2 | 11/2011 | Bunschoten et al. |
| 8,071,729 B2 | 12/2011 | Giles-Komar et al. |
| 8,076,319 B2 | 12/2011 | Leonard |
| 8,088,605 B2 | 1/2012 | Beaudet et al. |
| 8,101,209 B2 | 1/2012 | Legrand et al. |
| 8,101,773 B2 | 1/2012 | Smith |
| 8,114,434 B2 | 2/2012 | Sasaki et al. |
| 8,158,614 B2 | 4/2012 | Lambert et al. |
| 8,182,833 B2 | 5/2012 | Hermsmeyer |
| 8,202,736 B2 | 6/2012 | Mousa et al. |
| 8,217,024 B2 | 7/2012 | Ahmed et al. |
| 8,222,008 B2 | 7/2012 | Thoene |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,273,730 B2 | 9/2012 | Fernandez et al. |
| 8,287,888 B2 | 10/2012 | Song et al. |
| 8,329,680 B2 | 12/2012 | Evans et al. |
| 8,349,820 B2 | 1/2013 | Zeun et al. |
| 8,420,111 B2 | 4/2013 | Hermsmeyer |
| 8,435,561 B2 | 5/2013 | Besins et al. |
| 8,658,628 B2 | 2/2014 | Baucom |
| 8,663,681 B2 | 3/2014 | Ahmed et al. |
| 2001/0005728 A1 | 6/2001 | Guittard et al. |
| 2001/0021816 A1 | 9/2001 | Caillouette |
| 2001/0027189 A1 | 10/2001 | Bennink et al. |
| 2001/0029357 A1 | 10/2001 | Bunt et al. |
| 2001/0031747 A1 | 10/2001 | DeZiegler et al. |
| 2001/0034340 A1 | 10/2001 | Pickar |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0058648 A1 | 5/2002 | Hammerly |
| 2002/0058926 A1 | 5/2002 | Rathbone et al. |
| 2002/0076441 A1 | 6/2002 | Shih et al. |

(56) References Cited

U.S. PATENT DOCUMENTS

| | | |
|---|---|---|
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0132801 A1 | 9/2002 | Heil et al. |
| 2002/0137749 A1 | 9/2002 | Levinson et al. |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0173510 A1 | 11/2002 | Levinson et al. |
| 2002/0193356 A1 | 12/2002 | Van Beek et al. |
| 2003/0004145 A1 | 1/2003 | Leonard |
| 2003/0007994 A1 | 1/2003 | Bunt et al. |
| 2003/0049307 A1 | 3/2003 | Gyurik |
| 2003/0064097 A1 | 4/2003 | Patel et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225050 A1 | 12/2003 | Grawe et al. |
| 2003/0228686 A1 | 12/2003 | Klausner et al. |
| 2003/0229057 A1 | 12/2003 | Caubel et al. |
| 2004/0009960 A1 | 1/2004 | Heil et al. |
| 2004/0034001 A1 | 2/2004 | Karara |
| 2004/0037881 A1 | 2/2004 | Guittard et al. |
| 2004/0043943 A1 | 3/2004 | Guittard et al. |
| 2004/0044080 A1 | 3/2004 | Place et al. |
| 2004/0052824 A1 | 3/2004 | Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0089308 A1 | 5/2004 | Welch |
| 2004/0092583 A1 | 5/2004 | Shanahan-Prendergast |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0131670 A1 | 7/2004 | Gao |
| 2004/0142012 A1 | 7/2004 | Bunt et al. |
| 2004/0146894 A1 | 7/2004 | Warrington et al. |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191276 A1 | 9/2004 | Muni |
| 2004/0198706 A1 | 10/2004 | Carrara |
| 2004/0213744 A1 | 10/2004 | Lulla et al. |
| 2004/0234606 A1 | 11/2004 | Levine et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0004088 A1 | 1/2005 | Hesch |
| 2005/0009800 A1 | 1/2005 | Thumbeck et al. |
| 2005/0020552 A1 | 1/2005 | Aschkenasy et al. |
| 2005/0021009 A1 | 1/2005 | Massara et al. |
| 2005/0025833 A1 | 2/2005 | Aschkenasy et al. |
| 2005/0031651 A1 | 2/2005 | Gervais et al. |
| 2005/0042173 A1 | 2/2005 | Besse et al. |
| 2005/0042268 A1 | 2/2005 | Aschkenasy et al. |
| 2005/0048116 A1 | 3/2005 | Straub et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118272 A1 | 6/2005 | Besse et al. |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0207990 A1 | 9/2005 | Funke et al. |
| 2005/0214384 A1 | 9/2005 | Juturu et al. |
| 2005/0220825 A1 | 10/2005 | Funke et al. |
| 2005/0222106 A1 | 10/2005 | Bracht |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0271598 A1 | 12/2005 | Friedman et al. |
| 2005/0272712 A1 | 12/2005 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0083778 A1 | 4/2006 | Allison et al. |
| 2006/0089337 A1 | 4/2006 | Casper et al. |
| 2006/0093678 A1 | 5/2006 | Chickering, III et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0194775 A1 | 8/2006 | Tofovic et al. |
| 2006/0204557 A1 | 9/2006 | Gupta et al. |
| 2006/0235037 A1 | 10/2006 | Purandare et al. |
| 2006/0240111 A1 | 10/2006 | Fernandez et al. |
| 2006/0247216 A1 | 11/2006 | Haj-Yehia |
| 2006/0252049 A1 | 11/2006 | Shuler et al. |
| 2006/0257472 A1 | 11/2006 | Nielsen |
| 2006/0275360 A1 | 12/2006 | Ahmed et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2007/0004693 A1 | 1/2007 | Woolfson et al. |
| 2007/0004694 A1 | 1/2007 | Woolfson et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0178166 A1 | 8/2007 | Bernstein et al. |
| 2007/0184558 A1 | 8/2007 | Roth et al. |
| 2007/0191319 A1 | 8/2007 | Ke et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0238713 A1 | 10/2007 | Gast et al. |

(56) References Cited

U.S. PATENT DOCUMENTS

| | | |
|---|---|---|
| 2007/0243229 A1 | 10/2007 | Smith et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | DeVries et al. |
| 2007/0287789 A1 | 12/2007 | Jones et al. |
| 2007/0292387 A1 | 12/2007 | Jon et al. |
| 2008/0026035 A1 | 1/2008 | Chollet et al. |
| 2008/0026062 A1 | 1/2008 | Farr et al. |
| 2008/0038350 A1 | 2/2008 | Gerecke et al. |
| 2008/0085877 A1 | 4/2008 | Bortz |
| 2008/0095838 A1 | 4/2008 | Abou Chacra-Vernet |
| 2008/0113953 A1 | 5/2008 | De Vries et al. |
| 2008/0114050 A1 | 5/2008 | Fensome et al. |
| 2008/0119537 A1 | 5/2008 | Zhang et al. |
| 2008/0125402 A1 | 5/2008 | Diliberti et al. |
| 2008/0138379 A1 | 6/2008 | Jennings-Spring |
| 2008/0145423 A1 | 6/2008 | Khan et al. |
| 2008/0175814 A1 | 7/2008 | Phiasivongsa et al. |
| 2008/0188829 A1 | 8/2008 | Creasy |
| 2008/0206161 A1 | 8/2008 | Tamarkin et al. |
| 2008/0220069 A1 | 9/2008 | Allison |
| 2008/0234199 A1 | 9/2008 | Katamreddym |
| 2008/0255078 A1 | 10/2008 | Katamreddym |
| 2008/0255089 A1 | 10/2008 | Katamreddym |
| 2008/0299220 A1 | 12/2008 | Tamarkin et al. |
| 2008/0306036 A1 | 12/2008 | Katamreddym |
| 2008/0312197 A1 | 12/2008 | Rodriguez |
| 2008/0312198 A1 | 12/2008 | Rodriguez |
| 2008/0319078 A1 | 12/2008 | Katamreddym |
| 2009/0053294 A1 | 2/2009 | Prendergast |
| 2009/0060982 A1 | 3/2009 | Ron et al. |
| 2009/0068118 A1 | 3/2009 | Eini et al. |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0099106 A1 | 4/2009 | Phiasivongsa et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0181088 A1 | 7/2009 | Song et al. |
| 2009/0214474 A1 | 8/2009 | Jennings |
| 2009/0227025 A1 | 9/2009 | Nichols et al. |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0318558 A1 | 12/2009 | Kim et al. |
| 2009/0325916 A1 | 12/2009 | Zhang et al. |
| 2010/0028360 A1 | 2/2010 | Atwood |
| 2010/0040671 A1 | 2/2010 | Ahmed et al. |
| 2010/0048523 A1 | 2/2010 | Bachman et al. |
| 2010/0303825 A9 | 2/2010 | Sirbasku |
| 2010/0074959 A1 | 3/2010 | Hansom et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate |
| 2010/0184736 A1 | 7/2010 | Coelingh Bennink et al. |
| 2010/0190758 A1 | 7/2010 | Fauser et al. |
| 2010/0240626 A1 | 9/2010 | Kulkarni et al. |
| 2010/0247632 A1 | 9/2010 | Dong et al. |
| 2010/0255085 A1 | 10/2010 | Liu et al. |
| 2010/0312137 A1 | 12/2010 | Gilmour et al. |
| 2010/0316724 A1 | 12/2010 | Whitfield et al. |
| 2010/0330168 A1 | 12/2010 | Gicquel et al. |
| 2011/0028439 A1 | 2/2011 | Witt-Enderby et al. |
| 2011/0053845 A1 | 3/2011 | Levine et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0091555 A1 | 4/2011 | De Luigi Bruschi et al. |
| 2011/0098631 A1 | 4/2011 | Mcintyre et al. |
| 2011/0104289 A1 | 5/2011 | Savoir Vilboeuf et al. |
| 2011/0135719 A1 | 6/2011 | Besins et al. |
| 2011/0182997 A1 | 7/2011 | Lewis et al. |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0250274 A1 | 10/2011 | Shaked et al. |
| 2011/0256092 A1 | 10/2011 | Phiasivongsa et al. |
| 2011/0262494 A1 | 10/2011 | Achleitner et al. |
| 2011/0268665 A1 | 11/2011 | Tamarkin et al. |
| 2011/0293720 A1 | 12/2011 | General et al. |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2012/0009276 A1 | 1/2012 | De Groote |
| 2012/0015350 A1 | 1/2012 | Nabatiyan et al. |
| 2012/0045532 A1 | 2/2012 | Cohen |
| 2012/0269878 A2 | 2/2012 | Cantor et al. |
| 2012/0052077 A1 | 3/2012 | Truitt et al. |
| 2012/0128625 A1 | 5/2012 | Shalwitz et al. |
| 2012/0128777 A1 | 5/2012 | Keck et al. |
| 2012/0149748 A1 | 6/2012 | Shanler et al. |
| 2012/0269721 A1 | 10/2012 | Weng et al. |
| 2012/0283671 A1 | 11/2012 | Shibata et al. |
| 2013/0022674 A1 | 1/2013 | Dudley et al. |
| 2013/0029947 A1 | 1/2013 | Nachaegari et al. |
| 2013/0129818 A1 | 5/2013 | Bernick et al. |

FOREIGN PATENT DOCUMENTS

| | | |
|---|---|---|
| EP | 0785212 A1 | 7/1997 |
| EP | 1094781 B1 | 7/2008 |
| EP | 2191833 A1 | 6/2010 |
| GB | 1589946 A1 | 2/1921 |
| GB | 452238 A | 8/1936 |
| GB | 720561 A | 12/1954 |
| GB | 848881 A | 9/1960 |
| GB | 874368 A | 8/1961 |
| IN | 216026 A | 3/2008 |
| IN | 2005KO00053 A | 9/2009 |
| IN | 244217 A | 11/2010 |
| WO | 9011064 A1 | 10/1990 |
| WO | 9317686 A1 | 9/1993 |
| WO | 9422426 A1 | 10/1994 |
| WO | 9530409 A1 | 11/1995 |
| WO | 9609826 A2 | 4/1996 |
| WO | 9630000 A1 | 10/1996 |
| WO | 9705491 | 2/1997 |
| WO | 9743989 A1 | 11/1997 |
| WO | 9810293 A1 | 3/1998 |
| WO | 9832465 A1 | 7/1998 |
| WO | 9851280 A1 | 11/1998 |
| WO | 9932072 A1 | 7/1999 |
| WO | 9939700 A1 | 8/1999 |
| WO | 9942109 A1 | 8/1999 |
| WO | 9943304 | 9/1999 |
| WO | 9948477 A1 | 9/1999 |
| WO | 9953910 A2 | 10/1999 |
| WO | 0038659 A1 | 11/1999 |
| WO | 9963974 A2 | 12/1999 |
| WO | 0001351 A1 | 1/2000 |
| WO | 0006175 A1 | 2/2000 |
| WO | 0045795 A2 | 8/2000 |
| WO | 0050007 A1 | 8/2000 |
| WO | 0059577 A1 | 10/2000 |
| WO | 0137808 A1 | 11/2000 |
| WO | 0076522 A1 | 12/2000 |
| WO | 0154699 A1 | 8/2001 |
| WO | 0160325 A1 | 8/2001 |
| WO | 0207700 A2 | 2/2002 |
| WO | 0211768 A1 | 2/2002 |
| WO | 0222132 A2 | 3/2002 |
| WO | 0240008 A2 | 5/2002 |

(56) References Cited

FOREIGN PATENT DOCUMENTS

| | | |
|---|---|---|
| WO | 02053131 A1 | 7/2002 |
| WO | 02078602 A2 | 10/2002 |
| WO | 2002078604 A2 | 10/2002 |
| WO | 03041718 A1 | 5/2003 |
| WO | 03041741 A1 | 5/2003 |
| WO | 03068186 A1 | 8/2003 |
| WO | 03077923 A1 | 9/2003 |
| WO | 03082254 A1 | 10/2003 |
| WO | 03092588 A2 | 11/2003 |
| WO | 2004017983 A1 | 3/2004 |
| WO | 2005027911 A1 | 3/2004 |
| WO | 2004032897 A2 | 4/2004 |
| WO | 2004052336 A2 | 6/2004 |
| WO | 2004054540 A2 | 7/2004 |
| WO | 2004080413 A2 | 9/2004 |
| WO | 2005030175 A1 | 4/2005 |
| WO | 2005087194 A1 | 9/2005 |
| WO | 2005087199 A2 | 9/2005 |
| WO | 2005105059 A1 | 11/2005 |
| WO | 2005115335 A1 | 12/2005 |
| WO | 2005120470 A1 | 12/2005 |
| WO | 2005120517 A1 | 12/2005 |
| WO | 2006013369 A2 | 2/2006 |
| WO | 2006034090 A1 | 3/2006 |
| WO | 2006036899 A2 | 4/2006 |
| WO | 2006053172 A2 | 5/2006 |
| WO | 2006105615 A1 | 10/2006 |
| WO | 2006113505 A2 | 10/2006 |
| WO | 2006138686 A1 | 12/2006 |
| WO | 2006138735 A2 | 12/2006 |
| WO | 2007045027 A1 | 4/2007 |
| WO | 2007103294 A2 | 9/2007 |
| WO | 2007123790 A1 | 11/2007 |
| WO | 2007124250 A2 | 11/2007 |
| WO | 2007144151 A1 | 12/2007 |
| WO | 2008049516 A3 | 5/2008 |
| WO | 2008152444 A2 | 12/2008 |
| WO | 2009002542 A1 | 12/2008 |
| WO | 2009036311 A1 | 3/2009 |
| WO | 2009040818 | 4/2009 |
| WO | 2009069006 A2 | 6/2009 |
| WO | 2009098072 A2 | 8/2009 |
| WO | 2009133352 A2 | 11/2009 |
| WO | 2010033188 A2 | 3/2010 |
| WO | 2011000210 A1 | 1/2011 |
| WO | 2011073995 A2 | 6/2011 |
| WO | 2011120084 A1 | 10/2011 |
| WO | 2011128336 A1 | 10/2011 |
| WO | 2012009778 A2 | 1/2012 |
| WO | 2012024361 A1 | 2/2012 |
| WO | 2013192248 A1 | 12/2013 |
| WO | 2013192249 A1 | 12/2013 |
| WO | 2013192250 A1 | 12/2013 |
| WO | 2013192251 A1 | 12/2013 |

OTHER PUBLICATIONS

International Search Report and Written Opinion for related International Application No. PCT/US12/066406 dated Jan. 24, 2013.
International Search Report and Written Opinion for related International Application No. PCT/US13/023309 dated Apr. 9, 2013.
International Search Report and Written Opinion for related International Application No. PCT/US13/046442 dated Nov. 1, 2013.
International Search Report and Written Opinion for related International Application No. PCT/US13/046443 dated Oct. 31, 2013.
International Search Report and Written Opinion for related International Application No. PCT/US13/046444 dated Oct. 31, 2013.
International Search Report and Written Opinion for related International Application No. PCT/US13/046445 dated Nov. 1, 2013.
USPTO; Non-Final Office Action dated Mar. 20, 2013 for U.S. Appl. No. 13/684,002.
USPTO; Final Office Action dated Jul. 16, 2013 for U.S. Appl. No. 13/684,002.
USPTO; Notice of Allowance dated Dec. 6, 2013 for U.S. Appl. No. 13/684,002.
Acarturk, "Mucoadhesive Vaginal Drug Delivery Systems," Gazi University, Faculty of Pharmacy, Department of Pharmaceutical Technology, Exiler-Ankara, Recent Patents on Drug Delivery & Formulation 2009, 3, 193-205.
Azeem et al., "Microemulsions as a Surrogate Carrier for Dermal Drug Delivery," Drug Development and Industrial Pharmacy, 35(5):525-547 (May 2009). Abstract Only.
Azure Pharma, Inc., "ELESTRIN™—Estradiol Gel" Drug Info, http://dailymed.nlm.nih.gov/dailymed/archives/fdaDrugInfo.cfm?archiveid=11885, 26 pages (Aug. 2009).
Bhavnani, et al., "Structure Activity Relationships and Differential Interactions and Functional Activity of Various Equine Estrogens Mediated via Estrogen Receptors (ERs) ERa and ERb", Endocrinology, 149(10): 4857-4870 (Oct. 2008).
Bhavnani, et al., "Misconception and Concerns about Bioidentical Hormones Used for Custom-Compounded Hormone Therapy," J Clin Endocrinol Metab, Mar. 2012, 97(3).
Tahition Noni, "Body Balance Cream," http://products.tni.com/dominican_republic/sa_spanish/nonistore/product/3438/3416/, (undated), 1 page.
Nugen, "What is NuGen HP Hair Growth System?" http://www.skinenergizer.com/Nugen-HP-Hair-Growth-System-p/senusystem.htm, (undated), 3 pages.
Chun et al., "Transdermal Delivery of Estradiol and Norethindrone Acetate: Effect of Vehicles and Pressure Sensitive Adhesive Matrix," J. Kor. Pharm. Sci., 35(3):173-177, (2005).
Committee of Obstetric Practice, Committee Opinion—No. 522, Obstetrics & Gynecology, 119(4):879-882 (Apr. 2012).
Diramio, "Polyethylene Glycol Methacrylate/Dimetacrylate Hydrogels for Controlled Release of Hydrophobic Drugs," The University of Georgia-Masters of Science Thesis, 131 pages (2004). http://athenaeum.libs.uga.edu/bitstream/handle/10724/7820/diramio_jackie_a_200412_ms.pdf?sequence=1.
Du, et al. "Percutaneous Progesterone Delivery Via Cream or Gel Application in Postmenopausal Women: A Randomized Cross-Over Study of Progesterone Levels in Serum, Whole Blood, Saliva, and Capillary Blood," Menopause: The Journal of The North American Menopause Society, vol. 20, No. 11, (Feb. 2013).
Fotherby, K., "Bioavailability of Orally Administered Sex Steroids Used in Oral Contraception and Hormone Replacement Therapy," Contraception 1996;54:59-69.
Fuchs, et al., "The Effects of on Estrogen ond Glycolic Acid Creom on the Fociol Skin of Postmenopousol Women: A Rondomized Histologic Study," Pharmacology / Cosmetology, vol. 5, No. 1, 2006.
Ganem-Quintanar et al., "Evaluation of the transepidermal permeation of diethylene glycol monoethyl ether and skin water loss," International Journal of Pharmaceutics, 147(2):165-171 (Feb. 1997). Abstract Only.
Hargrove, et al., Menopausal Hormone Replacement Therapy With Continuous Daily Oral Micronized Estradiol and Progesterone, vol. 73, No. 4, pp. 606-612 Apr. 1989.
Johanson, "Toxicity Review of Ethylene Glycol Monomethyl Ether and its Acetate Ester," Critical Reviews in Toxicology, 30(3):307-345 (2000).
Kincl, et al., "Increasing Oral Bioavailability of Progesterone by Formulation," Pergamon Press, Journal of Steroid Biochemistry, 1978, vol. 9, pp. 83-84.
Knuth et al., "Hydrogel Delivery Systems for Vaginal and Oral Applications: Formulation and Biological Considerations," Advanced Drug Delivery Reviews, 11(1-2):137-167 (Jul.-Aug. 1993). Abstract Only.
Lucy et al., "Gonadotropin-Releasing Hormone at Estrus: Luteinizing Hormone, Estradiol, and Progesterone During the Periestrual and Postinsemination Periods in Dairy Cattle," Biol Reprod. 35(2):300-311 (1986). Abstract Only.
Position Statement, "Management of Symptomatic Vulvovaginal Atrophy: 2013 Position Statement of the North American Menopause Society," Menopause: The Journal of the North American Menopause Society, vol. 20, No. 9, pp. 888-902, Jun. 2013.
NuGest 900™, http://www.thehormoneshop.net/nugest900.htm, (undated), 4 pages.

(56) References Cited

OTHER PUBLICATIONS

Panay, et al., "The 2013 British Menopause Society & Women's Health Concern Recommendations on Hormone Replacement Therapy," DOI: 0.1177/1754045313489645, min.sagepub.com. Menopause International: The Integrated Journal of Postreproductive Health 0(0):1-10, 2013.
Panchagnula et al., "Development and Evaluation of an Intracutaneous Depot Formulation of Corticosteroids Using Transcutol as a Cosolvent: In-Vitro, Ex-Vivo and In-Vivo Rat Studies," J Pharm Pharmacol. 43(9):609-614 (Sep. 1991). Abstract Only.
Patel, et al., "Transdermal Drug Delivery System: A Review," www.thepharmajournal.com, vol. 1 No. 4 2012.
Salole, "The physiochemical properties of oestradiol," Journal of Pharmaceutical & Biomedical Analysis, 5 (7):635-648 (1987).
Sarrel, et al., "The Mortality Toll of Estrogen Avoidance: An Analysis of Excess Deaths Among Hysterectomized Women Aged 50 to 59 Years," American Journal of Public Health, Published online ahead of print Jul. 18, 2013.
Shufelt, et al., "Hormone Therapy Dose, Formulation, Route of Delivery, and Risk of Cardiovascular Events in Women: Findings From the Women's Health Initiative Observational Study," Menopause: The Journal of the North American Menopause Society, vol. 21, No. 3, 2014.
Simon, et al., "Effective Treatment of Vaginal Atrophy With an Ultra-Low-Dose Estradiol Vaginal Tablet," The American College of Obstetricians and Gynecologists, vol. 112, No. 5, Nov. 2008.
Sitruk-Ware, et al., "Oral Micronized Progesterone," Department of Reproductive Endocrinology, vol. 36, No. 4, pp. 373-402, Oct. 1987.
Sitruk-Ware, et al., "Progestogens in Hormonal Replacement Therapy: New Molecules, Risks, and Benefits," Menopause: The Journal of the North American Menopause Society, vol. 9, No. 1, pp. 6-15, 2002.
Smith, et al., "Lower Risk of Cardiovascular Events in Postmenopausal Women Taking Oral Estradiol Compared With Oral Conjugated Equine Estrogens," JAMA Internal Medecine http://archinte.jamanetwork.com, Sep. 30, 2013.
Stanczyk, et al. "Ethinyl Estradiol and 17β-Estradiol in Combined Oral Contraceptives: Pharmacokinetics, Pharmacodynamics and Risk Assessment," Departments of Obstetrics and Gynecology and Preventive Medicine, University of Southern California Keck School of Medicine, Contraception 87 706-727, (2013).
Strickley, "Solubilizing Excipients in Oral and Injectable Formulations," Pharmaceutical Research,21(2):201-230 (Feb. 2004).
Trommer et al., "Overcoming the Stratum Corneum: The Modulation of Skin Penetration," Skin Pharmacol Physiol, 19:106-121 (2006). http://www.nanobiotec.iqm.unicamp.br/download/Trommer_skin%20penetration-2006rev.pdf.
Whitehead, et al., "Absorption and Metabolism of Oral Progesterone," The British Medical Journal, vol. 280, No. 6217, Mar. 22, 1980.
Wood, et al., "Effects of Estradiol with Micronized Progesterone or Medroxyprogesterone Acetate on Risk Markers for Breast Cancer in Postmenopausal Monkeys," Springer Science+Business Media B.V., Breast Cancer Res Treat 101:125-134, (2007).
USPTO; Non-Final Office Action dated Feb. 18, 2014 for U.S. Appl. No. 14/099,545.
USPTO; Restriction/ Election Requirement dated Feb. 20, 2014 for U.S. Appl. No. 14/099,562.
USPTO; Restriction/ Election Requirement dated Mar. 5, 2014 for U.S. Appl. No. 14/099,623.
Kubli-Garfias, C, et al., Ab initio calculations of the electronic structure of glucocorticoids, Jour. of Mol. Structure, Theochem, vol. 454 pp. 267-275, 1998, Elsevier.
Kubli-Garfias, Carlos, Ab initio study of the electronic structure of progesterone and related progestins, Jour. of Mol. Structure, Theochem vol. 425, pp. 171-179, 1998, Elsevier.
Kuhnert-Brandstaetter, M & Kofler, A, Zur Unterscheidung von losungsmittelhaltigen pseudopolymorphen Kristallformen and polymorphen Modifikationen bei Steroidhormonen.II. vol. 1 pp. 127-139, 1968, Mikrochimica Acta.
Kuhnert-Brandstaetter, M & Lnder, R, Zur Hydratbildung bei Steroidhormonen, Sci. Pharm., vol. 41(2) pp. 109-116, 1973.
Kuhnert-Brandstatter, M, Thermo-microscopic and spectrophotometric: Determination of steroid hormones, Microchemical Journal 9, pp. 105-133, 1965.
Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.
Lacey, J.V. Jr., The WHI ten year's later: An epidemiologist's view, J. Steroid Biochem. Mol. Biol. (2013), Elsevier.
Lahiani-Skiba, Malika, Solubility and Dissolution Rate of Progesterone-Cyclodextrin . . . , Drug Development and Industrial Pharmacy, Informa Healthcare vol. 32, pp. 1043-1058, 2006.
Lancaster, Robert W, et al., The Polymorphism of Progesterone: Stabilization of a 'Disappearing' Polymorph by . . . , Jour. of Pharm. Sci., vol. 96(12) pp. 3419-31, 2007, Wiley-Liss.
Land, Laura M, The influence of water content of triglyceride oils on the solubility of steriods, Pharmaceutical Research, vol. 22(5) May 2005, Springer Science+Business Media.
Leonetti, Helene B, et al., Topical progesterone cream has an antiproliferative effect on estrogen-stimulated endometrium, Fertility and Sterility, vol. 79(1), Jan. 2003.
Lewis, John G., et al., Caution on the use of saliva measurements to monitor absorption of progesterone . . . , Maturitas, The European Menopaus Journal, vol. 41, pp. 1-6, 2002.
Li, Guo-Chian, Solid-state NMR analysis of steroidal conformation of 17a- and 17B-estradiol in the absence and presence of lipi . . . , Steroids, Elsevier, vol. 77, pp. 185-92, 2012.
Lobo, R.A., Foreword, J. Steroid Biochem. Mol. Biol. (2014), Elsevier.
Lvova, M. SH., et al., Thermal Analysis in the Quality Control and Standardization of Some Drugs, J Thermal Anal., vol. 40 pp. 405-411, 1993, Wiley.
Magness, R.R., et al., Estrone, Estradiol-17b and Progesterone Concentrations in Uterine Lymph and Systematic Blood . . . , Journal of Animal Science, vol. 57, pp. 449-455, ISU, 1983.
McGuffy, Irena, Softgel Technology as a Lipid-Based Delivery Tool for Bioavailability Enhancement, Catalent Pharma Solutions, Somerset, NJ, Mar. 2011.
Merck Index Online, Progesterone, Royal Society of Chemistry, 2013, search Feb. 17, 2014 https://www.rsc.org/Merck-Index/monograph/print/mono1500007889/progesterone?q=authorize.
Merck Index Online, Progesterone, Royal Society of Chemistry, 2013, search Feb. 24, 2014 https://www.rsc.org/Merck-Index/monograph/print/mono1500007889/progesterone?q=authorize.
Merck Index, Estradiol, The Merck Index Online, Royal Society of Chemistry 2014, MONO1500003758.
Mesley, R.J., Clathrate Formation from Steroids, Chemistry and Industry, vol. 37 pp. 1594-1595, Sep. 1965.
Miao, Wenbin, et al., Chemical Properties of Progesterone, SciFinder, 2014, American Chemical Society & US Natl. Lib. of Med.
Mueck, A.O., et al., Genomic and non-genomic actions of progestogens in the breast, J. Steroid Biochem. Mol.Biol. (2013), Elsevier.
Muramatsu, Mitsuo, Thermodynamic Relationship between a- and B- Forms of Crystalline Progesterone, J. Pharmaceutical Sciences, vol. 68(2) pp. 175-178, 1979, Amer. Pharm. Assoc.
Nicklas, Martina, Preparation and characterization of marine sponge collagen nanoparticles and employment for the trans . . . , Drug Devel. & Indust. Pharmacy,35(9) pp. 1035, 2009.
O'Leary, Peter, Salivary, but not serum or urinary levels of progesterone are elevated after topical . . . , Clinical Endocrinology, vol. 53 pp. 615-620, Blackwell Science 2000.
Open Notebook, Science Solubility Challenge, Jul. 16, 2013, Solubility of progesterone in organic solvents, http://Ixsrv7.oru.edu/~alang/onsc/solubility/allsolvents.php?solute=progesterone.
Park, Jeong-Sook, Solvent effects on physicochemical behavior of estradiols recrystalized for transdermal delivery, Arch Pharm Res, vol. 31(1), pp. 111-116, 2008.

(56) References Cited

OTHER PUBLICATIONS

Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Payne, R.S., et al., Examples of successful crystal structure prediction: polymorphs of primidone and progesterone, Intl. Jour. of Pharma., vol. 177 pp. 231-45, 1999, Elsevier.
Persson, Linda C, et al., Physicochemical Properties of Progesterone Selecte, SciFinder, pp. 1-5, Feb. 24, 2014, American Chem. Society & US Natl. Lib. of Med.
Pheasant, Richard, Polymorphism of 17-Ethinylestradiol, Schering Corporation, Bloomfield, NJ, May 1950.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Price, Sarah L, The computational prediction of pharmaceutical crystal structures and polymorphism, Adv. Drug Delivery Reviews, vol. 56 pp. 301-319, 2004, Elsevier.
Progynova TS 100, available online at file:///C:/Users/Call%20Family/Desktop/Progynova%20TS%20100%2012%20Patches_Pack%20%28Estradiol%20Hemihydrate%29.html, 2010.
Rosilio, V, et al., Physical Aging of Progesterone-Loaded Poly(D,L,-lactide-co-glycolide) Microspheres, Pharmaceutical Research, vol. 15(5) pp. 794-799,1998, Plenum Pub. Corp.
Salole, Eugene G., Estradiol, Analytical Profiles of Drug Substances, vol. 15, pp. 283-318, 1986.
Santen, R.J., Menopausal hormone therapy and breast cancer, J. Steroid Biochem. Mol. Biol. (2013), Elsevier.
Sarkar, Basu, et al., Chemical Stability of Progesterone in Compounded Topical Preparations using PLO Transdermal Cream™ and HRT Cream™ Base . . . , J Steroids Horm Sci, 4:2, 2013.
Satyanarayana, D, et al., Aqueous Solubility Predictions of Aliphatic Alcohols, Alkyl Substituted Benzoates and Steroids, Asian J. Chem., vol. 9 (3) pp. 418-26, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Serantoni, Forest!, et al., 4-Pregnen-3,20-dione (progesterone, form II), Crystal Structure Comm., vol. 4(1) pp. 189-192, 1975, CAPLUS Database.
Sharma, H. C., et al., Physical Properties of Progesterone Selected Refer, SciFinder, pp. 1-5, Feb. 24, 2014, American Chem. Society & US Natl. Lib. of Med.
Sigma-Aldrich, Progesterone-Water Soluble: powder, BioReagent, suitable for cell culture), MSDS available online: http://www.sigmaaldrich.com/catalog/product/sigma/p7556, (2014).
ACOG, McKinlay, et al., Practice Bulletin, Clinical Management Guidelines for Obstetrician-Gynecologists, ACOG, No. 141, vol. 123, No. 1, Jan. 2014, Obstetrics & Gynecology.
Araya-Sibaja, Andrea Manela, et al., Chemical Properties of Progesterone Selected Refer., SciFinder, 2014, American Chemical Society & US Natl. Lib. of Med.
Araya-Sibaja, Andrea M.A., Morphology Study of Progesterone Polymorphs Prepared by Polymer-Induced Heteronucleation (PIHn), Scanning vol. 35 pp. 213-221, 2013, Wiley Period., Inc.

Araya-Sibaja, Andrea Manela, et al., Polymorphism in Progesterone, SciFinder, pp. 1-46, Feb. 24, 2014, American Chem. Society & Natl. Lib. of Med.
Araya-Sibaja, Andrea Manela, et al., Polymorphism in Progesterone Selected References, SciFinder, Feb. 24, 2014, pp. 1-12, American Chem. Society & Natl. Lib. of Med.
Bakhmutova-Albert, Ekaterina, et al., Enhancing Aqueous Dissolution Rates of Progesterone via Cocrystallization, SSCI, Division of Aptuit, Poster No. R6247, West Lafayette (2014).
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infared and solution Raman spectroscopic studies of 17B-estradiol and several A-ring . . . , Vibrational Spectroscopy 8, Elsevier, pp. 263, 1995.
Bernabei, M.T., et al., Release of progesterone polymorphs from dimethylpolysiloxane polymeric matrixes, Bollettino Chimico Farmaceutico, vol. 122(1) pp. 20-26, 1983 SciFinder.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central,Solubility of Progesterone in Organic Solvents, Online PDF, http://www.biomedcentral.com/content/supplementary/1475-2859-11-106-S2.pdf, (2014).
Borka, Laszlo, Crystal Polymorphism of Pharmaceuticals, Acta Pharm. Jugosl., vol. 40 pp. 71-94, 1990.
Brinton, L.A., Felix, A.S., Menopausal hormone therapy and risk of endometrial cancer, J. Steroid Biochem. Mol. Biol. (2013), Elsevier.
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Molcculaire de la Progesterone C21H30O2, Acta Cryst., B28 pp. 3032-3042, 1972.
Cendejas-Santana, G, et al., Growth and characterization of progesterone crystallites, Revista Mexicana de Fisica, 50, Suplemento 1 pp. 1-3, 2004.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Commodari, Fernando, Comparison of 17B-estradiol structures from x-ray diffraction and solution NMR, Magn. Reson. Chem., vol. 43, pp. 444-450, 2005, Wiley InterScience.
Cooper, A, et al., Systemic absorption of progesterone from Progest cream in postmenopausal women, The Lancet, vol. 351, pp. 1255-1256, Research Letters, Apr. 25, 1998.
Dideberg, O, et al., Crystal data on progesterone (C21H30O2), desoxycorticosterone (C21H30O3), corticosterone (C21H30O4) and aldosterone . . . , J. Appl. Cryst. vol. 4 pp. 80, 1971.
Drakulic, Branko J, Role of complexes formation between drugs and penetration enhancers in transdermal . . . , Inter. Journal of Pharmaceutics, Elsevier, vol. 363, pp. 40-49, 2009.
Duax, William L, et al., Conformation of Progesterone Side Chain: Conflict between X-ray Data and Force-Field Calculations, J. Am. Chem. Soc., vol. 103 pp. 6705-6712, Jun. 1981.
Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.

(56) References Cited

OTHER PUBLICATIONS

Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Freedman, R.R., Menopausal hot flashes: Mechanisms, endocrinology, treatment, J. Steroid Biochem. Mol. Biol. (2013), Elsevier.
Fugh-Berman, Adriane, Bioidentical Hormones for Menopausal Hormone Therapy: Variation on a Theme, Journal of General Internal Medicine, vol. 22, pp. 1030-1034, 2007.
Giron, D, Thermal analysis and calorimetric methods in the characterisation of polymorphs and solvates, Thermochimica Acta, vol. 248 pp. 1-59, 1995, Elsevier.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Gurney, E.P., et al., The Women's Health Initiative trial and related studies: 10 years later: A clinician's view, J. Steroid Biochem. Mol. Biol. (2013), Elsevier.
Haner, Barbara A., Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Helbling, Ignacio M, et al., The Optimization of an Intravaginal Ring Releasing Progesterone Using a Mathematical Model, Pharm Res, vol. 31 pp. 795-808, 2014, Springer Science.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Hodis, H.N., Mack, W.J., Hormone replacement therapy and the association with heart disease and overall mortality: Clinical . . . , J. Steroid Biochem. Mol. Biol. (2013), Elsevier.
Hospital, Michel, et al., X-ray Crystallography of Estrogens and Their Binding to Receptor Sites, Mol. Pharmacology, vol. 8 pp. 438-445, Acedemic Press, Inc., 1972.
Hulsmann, Stefan, Stability of Extruded 17B-Estradiol Solid Dispersions, Pharmaceutical Development and Tech., vol. 6(2) pp. 223-229, 2001, Marcel Dekker, Inc.
Idder, Salima, et al., Physicochemical properties of Progesterone, SciFinder, pp. 1-26, Feb. 24, 2014, American Chem. Society & US Natl. Lib. of Med.
Johnson, William S, et al., Racemic Progesterone, Tetrahedron Letters No. 4, pp. 193-196, 1963, Pergamon Press Ltd., Great Britain.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.
Korkmaz, Filiz, Byophysical Studies of Progesterone-Model Membrane Interactions, Thesis, Grad. School of Nat. and App. Sci. of the Middle East Tech. University, Sep. 2003.
Kotiyan, P.N., Stability indicating HPTLC method for the estimation of estradiol, Journal of Pharmaceutical and Biomedical Analysis, vol. 22 pp. 667-6671, 2000, Elsevier.
Krzyminiewski, R, et al., EPR Study of the Stable Radical in a y-radiated Single Crystal of Progesterone, Jour. of Mag. Resonance, vol. 46 pp. 300-305, 1982, Acedemic Press.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Alabi, K. A., et al., Analysis of Fatty Acid Composition of *Thevetia peruviana* and *Hura crepitans* Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
British Pharmacopocia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index[Feb. 3, 2014 1:37:50 PM].
ChemPro, Top-Notch Technology in Production of Oils and Fats, Chempro-Edible-Oil-Refining-ISO-TUV-Austria, (2014).
Corn Refiners Assoc, Corn Oil, 5th Edition, Washington, D.C., 2006.
Dauqan, Eqbal M. A, et al., Fatty Acids Composition of Four Different Vegetable Oils (Red Palm Olein, Palm Olein, Corn Oil, IPCBEE, vol. 14, 2011, IACSIT Press, Singapore.
Ferrari, Roseli AP., et al., Oxidative Stability of Biodiesel From Soybean Oil Fatty Acid Ethyl Esters, Sci. Agric., vol. 62(3), pp. 291-295, 2005, Piracicaba, Braz.
Gunstone, Frank D, et al., Vegetable Oils in Food Technology: Composition, Properties and Uses, Blackwell Publishing, CRC Press, 2002.
Ng, Jo-Han, et al., Advances in biodiesel fuel for application in compression ignition engines, Clean Techn Environ Policy, vol. 12, pp. 459-493, 2010, Springer-Verlag.
Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.
Prajapati, Hetal N, et al., A comparative Evaluation of Mono-, Di- and Triglyceride of Medium Chain Fatty Acids by Lipid/SurfactantiWater, Springerlink.com, pp. 1-21, Apr. 2011.
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
USP, 401 Fats and Fixed Oils, Chemical Tests, Second Suplement to USP36-NF 31, pp. 6141-6151, 2013.
USP, Lauroyl Polyoxylglycerides, Saftey Data Sheet, US, 5611 Version #02, pp. 1-9, 2013.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
USP, USP Certificate-Corn Oil, Lot G0L404, Jul. 2013.
Weber, E.J., Corn Lipids, Cereal Chem., vol. 55(5), pp. 572-584, The American Assoc of Cereal Chem, Sep.-Oct. 1978.
Araya-Sibaja, et al., Crystallization of progesterone polymorphs using polymer-induced heteronucleation (PIHn) method, Drug Development and Industrial Pharmacy, Early Online, pp. 1-8, 2014, Informa Healthcare.
Stanczyk, F.Z., Bhavnanib, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stein, Emily A, et al., Progesterone Physical Properties, SciFinder, pp. 1-46, Mar. 3, 2014, American Chem. Society & US Natl. Lib. of Med.
Stein, Emily A, et al., Progesterone, SciFinder Scholar Search, pp. 1-46, Feb. 24, 2014, American Chem. Society & Natl. Lib. of Med.
Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Tait, Alex D, Characterization of the Prod. from the Oxidation of Progesterone with Osmium Tetroxide, Dept of Investigative Med., Univ. Cambridge, Gt. Britain pp. 531-542, 1972.

(56) References Cited

OTHER PUBLICATIONS

Takacs M, et al., The light sensitivity of corticosteroids in crystalline form, Pharmaceutica acta Helvetiae, vol. 66 (5-6) pp. 137-140, 1991, Hardin Library.

Tella, S.H., Gallagher, J.C., Prevention and treatment of postmenopausal osteoporosis, J. Steroid Biochem. Mol. Biol. (2013), Elsevier.

Thomas, Joshua, et al., The effect of water solubility of solutes on their flux through human skin in vitro: An . . . , Intl. J. of Pharmaceut., vol. 339 pp. 157-167, 2007, Elsevier.

Tripathi, R, et al., Study of Polymorphs of Progesterone by Novel Melt Sonocrystallization Technique: A Technical Note, AAPS PhamSciTech, vol. 11, No. 3, Sep. 2010.

USP Monographs: Progesterone, USP29, www.pharmacopeia.cn/v29240/usp29nf24s0__m69870.html, search done: Feb. 25, 2014.

Utian, Wulf H, et al., Relief of vasomotor symptoms and vaginal atrophy with lower doses of conjugated equine estrogens . . . Fertility and Sterility, vol. 75(6) pp. 1065, Jun. 2001.

Weber, M.T., et al., Cognition and mood in perimenopause: A systematic review and meta-analysis, J. SteroidBiochem. Mol. Biol. (2013), Elsevier.

Wiranidchapong, Chutima, Method of preparation does not affect the miscibility between steroid hormone and polymethacrylate, Thermochimica Acta 485, Elsevier, pp. 57, 2009.

Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.

Yue, W.,Genotoxic metabolites of estradiol in breast: potential mechanism of estradiol induced carcinogenesis, Journal of Steroid Biochem & Mol Biology, vol. 86 pp. 477-486, 2003.

PCCA, Apothogram, May 2014, pp. 1-14, Houston, TX.

US 6,214,374, 04/2001, Schmirler et al. (withdrawn)

* cited by examiner

NATURAL COMBINATION HORMONE REPLACEMENT FORMULATIONS AND THERAPIES

CROSS REFERENCE TO RELATED APPLICATIONS

This application is a non-provisional application of and claims priority to the following U.S. Provisional Patent Applications: U.S. Provisional Application Ser. No. 61/563,408, entitled "NATURAL COMBINATION HORMONE REPLACEMENT THERAPIES" which was filed on Nov. 23, 2011; U.S. Provisional Application Ser. No. 61/661,302, entitled "ESTRADIOL FORMULATIONS" which was filed on Jun. 18, 2012; and U.S. Provisional Application Ser. No. 61/662,265, entitled "PROGESTERONE FORMULATIONS" which was filed on Jun. 20, 2012. All aforementioned applications are hereby incorporated by reference herein in their entirety.

BACKGROUND

1. Field

This disclosure relates to natural estrogen and progesterone replacement therapies, with formulations provided for each estradiol and progesterone alone and in combination for the treatment of pre, peri-menopausal, menopausal and post-menopausal females in relation to the treatment of Estrogen- and Progesterone-deficient States, each as herein below defined.

2. Discussion of the Related Art

Hormone replacement therapy (HRT) is a medical treatment that involves the use of one or more of a group of medications designed to increase hormone levels in women who lack adequate hormone production. HRT can mitigate and preventsymptoms caused by diminished circulating estrogen and progesterone hormones regardless as to whether the subject is pre-menopausal, peri-menopausal, menopausal or post-menopausal. However, specific disease states can exist during each stage of menopausal progression.

HRT is presently available in various forms. One therapy involves administration of low dosages of one or more estrogens. Another involves administration of progesterone or a chemical analogue, called a progestin. Progesterone administration acts, among treating other disease states, to mitigate certain undesirable side effects from estrogen administration including, for example, endometrial hyperplasia (thickening), reducing the incidence of endometrial cancer.

Timing for dosage administration is often varied cyclically, with estrogens taken daily and progesterone taken for approximately two weeks of every month; a method often referred to as "Cyclic-Sequential" or "Sequentially-Combined HRT." This method is intended to mimic the natural menstrual cycle and typically causes menstruation similar to a period after the progesterone is stopped. This regimen is most typically used in peri-menopausal or newly menopausal women as the alternative continuous method often results in irregular bleeding in such women. An alternate method, a constant dosage with both estrogen and progesterone taken daily, is called "continuous-combined HRT." This method usually results in no menstruation and is used most often after a woman has been menopausal for some time.

Estrogen, in its various forms, and progesterone, in its various forms, are used in HRT via a variety of administered dosage forms including, for example, via tablets, capsules and patches.

"Bio-identical" hormones, which are identical in chemical structure to the hormones naturally produced by human bodies can be used and are often referred to as natural hormone replacement therapy, or NHRT.

These natural or bio-identical hormones are formulated from various ingredients to match the chemical structure and effect of estradiol, estrone, or estriol (the 3 primary estrogens) as well as progesterone that occur naturally in the human body (endogenous).

Currently, bio-identical estradiol is available in both branded and generic FDA approved versions. FDA-approved bio-identical progesterone for HRT is available as the branded stand-alone drug commercially identified as PROMETRIUM (progesterone, USP) (Abbott Laboratories, Abbott Park, Ill.), with a generic authorized by the innovator, and generic products provided by Teva (Israel) and Sofgen Americas, Inc (New York). Other products such as PREMPRO (conjugated estrogens/medroxyprogesterone acetate tablets) and PREMPHASE (conjugated estrogens plus medroxyprogesterone acetate tablets) (Wyeth Laboratories, a division Pfizer, Inc., New York) provide both continuous-combined and cyclic-sequential products containing PREMARIN (conjugated estrogens tablets) (estrogen derived from mare's urine) and synthetic medroxyprogesterone acetate. Other products are available. However, no FDA approved product exists on the market today with combination bio-identical estradiol and bio-identical progesterone.

SUMMARY

According to various embodiments of the disclosure, natural hormone replacement therapies are provided comprising cyclic/sequential and continuous-combined delivery via pharmaceutical formulations of solubilized estradiol and micronized and/or partially or completely solubilized progesterone. Estradiol and micronized and/or partially or completely solubilized progesterone delivered together daily can be combined in either a single unit dose or in separate unit doses, typically in a soft capsule. A 28-day or monthly regimen of tablets or capsules can be packaged in a single blister pack having delivery days identified to improve compliance. Various examples formulations of natural hormones, and the use of these formulations for hormone replacement therapies, each in accordance with the invention are set forth below.

BRIEF DESCRIPTION OF THE DRAWINGS/FIGURES

The accompanying drawings, which are incorporated herein and form a part of the specification, illustrate the present disclosure and, together with the description, further serve to explain the principles of the disclosure and to enable a person skilled in the pertinent art to make and use the disclosed embodiments.

DETAILED DESCRIPTION OF THE ILLUSTRATED EMBODIMENTS

Figure 1:
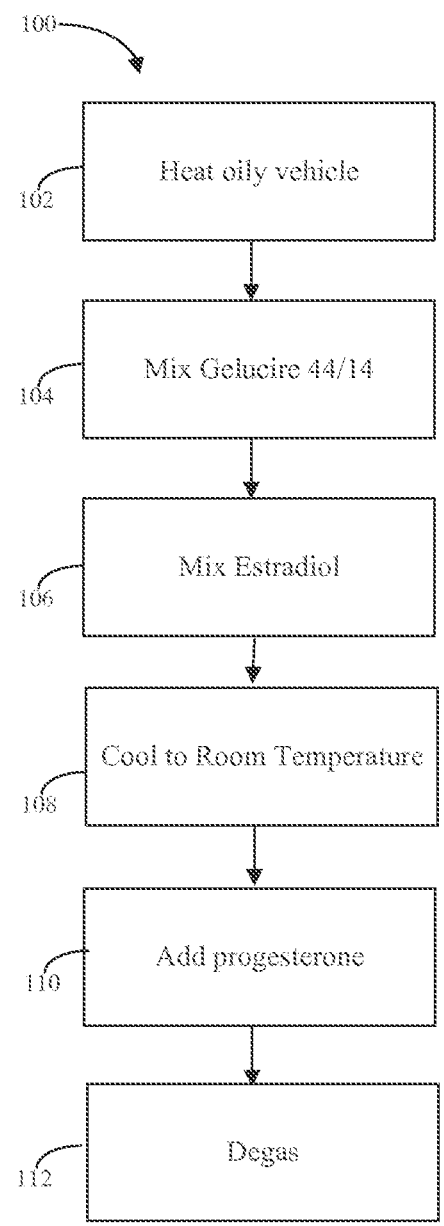
FIG. 1 illustrates an exemplary manufacturing process of a fill material in accordance with various embodiments.

Frequently, higher recommended oral dosages of pharmaceuticals are necessary to treat a given disease state because many active ingredients are not completely absorbed by a patient in need of treatment. In other words, a better-absorbed dosage form of a medicament such as, for example, progesterone, or dosage forms that provide greater consistency of absorption of progesterone among subjects, alone or in combination with estradiol, may be able to be administered at dosage strengths lower than presently recommended, potentially resulting in a reduced or minimized side effect profile, among other potential benefits.

Definitions

The term "micronized progesterone," as used herein, includes micronized progesterone having an X50 particle size value below about 15 microns and/or having an X90 particle size value below about 25 microns.

The term "X50," as used herein, means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "medium chain," as used herein means any medium chain carbon-containing substance, including C4-C18, and including C6-C12 substances, fatty acid esters of glycerol, fatty acids, and mono-, di-, and tri-glycerides of such substances.

The term "uniform distribution" means at least one of uniform dispersion, solubility, or lack of agglomeration of progesterone in a dissolution test compared to PROMETRIUM (progesterone, USP) at a similar dosage strength and the same USP dissolution apparatus.

The term "bioavailability," as used herein means the concentration of an active ingredient (e.g., progesterone or estradiol or estrone) in the blood (serum or plasma). The relative bioavailability may be measured as the concentration in the blood (serum or plasma) versus time. Other pharmacokinetic (pK) indicators may be used to measure and assess bioavailability, determined by suitable metrics including AUC, $C_{max}$, and optionally, $T_{max}$.

The term "AUC," as used herein, refers to the area under the curve that represents changes in blood concentration of progesterone, estradiol or estrone over time.

The term, "$C_{max}$" as used herein, refers to the maximum value of blood concentration shown on the curve that represents changes in blood concentrations of progesterone, estradiol or estrone over time.

The term, "$T_{max}$" as used herein, refers to the time that it takes for progesterone, estradiol or estrone blood concentration to reach the maximum value.

Collectively AUC, $C_{max}$ and, optionally, $T_{max}$ are the principle pharmacokinetic parameters that can characterize the pharmacokinetic responses of a particular drug product such as progesterone in an animal or human subject.

The term "solubilizer," as used herein, means any substance or mixture of substances that may be used to enhance the solubility of estradiol, including, for example and without limitation, appropriate pharmaceutically acceptable excipients, such as solvents, co-solvents, surfactants, emulsifiers, oils and carriers.

The term "excipients," as used herein, refer to non-active pharmaceutical ingredients ("API") substances such as carriers, solvents, oils, lubricants and others used in formulating pharmaceutical products. They are generally safe for administering to animals, including humans, according to established governmental standards, including those promulgated by the United States Food and Drug Administration.

The term "oil" as used herein may be any pharmaceutically acceptable substance, other than peanut oil, that would suspend and/or solubilize any suitable progesterone, starting material, or precursor, including micronized progesterone as described herein. More specifically, oils may include, for example and without limitation, medium chain fatty acids, generally of the group known as medium chain fatty acids consisting of at least one mono-, di-, and triglyceride, or derivatives thereof, or combinations thereof.

"Fully solubilized progesterone" as used herein means progesterone which is about 100% in solution.

"Partially solubilized progesterone" as used herein means progesterone which is in any state of solubilization up to but not including about 100%.

Description

Provided herein are the following formulations: solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; and solubilized estradiol with solubilized progesterone. The underlying formulation concepts provided herein may be used with other natural or synthetic forms of estradiol and progesterone. Micronization specifications, aspects and embodiments are further defined herein.

Generally, the pharmaceutical formulations described herein are prepared and administered as filled capsules, typically soft capsules of one or more materials well known in the art including, for example and without limitation, soft gelatin capsules. Micronized progesterone, as described herein, may also be prepared for administration in tablets or other well-known orally administered dosage forms using standard techniques.

Another aspect of the present disclosure includes a pharmaceutical formulation of micronized progesterone, micronized progesterone with partially solubilized progesterone and fully solubilized progesterone, wherein said formulation may provide increased progesterone bioavailability in a treated subject compared to the bioavailability provided by PROMETRIUM (progesterone, USP) when administered at equal dosage strengths.

In accordance with various aspects and embodiments, the solubility proportion (i.e., the proportion of a solute that enters solution) is notable. The weight ratio of estradiol to the weight of the entire solution is also notable due to the intended dose amounts, discussed herein. In particular, it is desirable to obtain a target dosage of estradiol in an amount of solution that may be readily administered via a capsule. For example, if it is desired to have a dose of estradiol in a capsule of between about 0.125 mg to about 2 mg, it would also be desirable to have a total solution weight to be between about 250 mg to about 400 mg, preferably about 300 mg to about 350 mg and more preferably about 325 mg. In various embodiments, the following weight ratios of estradiol to total solution is from about 0.125/50 mg to about 0.125/1000 mg, from about 1 mg:500 mg to about 1 mg:50 mg; from about 1 mg:250 mg to about 1 mg:60 mg; from about 1 mg:100 mg to about 1 mg:66 mg; from about 2 mg/50 mg to about 2 mg/1000 mg. In various embodiments, the target for single dose product is 325 mg, and a target fill weight for a combination product (e.g., two or more sterol APIs) is 650 mg.

Other aspects of the present disclosure further provide: more uniform dissolution of progesterone, and reduced intra- and inter-patient blood level variability in formulations of progesterone of the present disclosure, typically in combinations with solubilized estradiol, when compared to equal dosages of PROMETRIUM (progesterone, USP). Blood level variability is also compared at equal sampling times following administration. Not to be limited by theory, these aspects are believed to be influenced by the percentage of solubilized progesterone in a respective formulation wherein such more uniform dissolution of progesterone, and lower intra- and inter-patient blood level variability, are influenced by a greater proportion of solubilized progesterone relative to total progesterone. A reduced food effect with the present formulations comprising progesterone may also be implicated.

More uniform dissolution of progesterone in a formulation of the present disclosure compared to the dissolution of PROMETRIUM (progesterone, USP) at equal dosage strengths and using the same USP apparatus can be determined using standard techniques established for API dissolution testing, including that which is described in the examples below.

Reduced intra- and inter-patient variability of progesterone formulated pursuant to the present disclosure compared to PROMETRIUM (progesterone, USP) can be demonstrated via a fed bio-study such as that described below.

Other aspects of the present disclosure includes the use of formulations as described herein wherein progesterone is at least one API in said formulation for the treatment of an animal, including humans: for endometrial hyperplasia; for secondary amenorrhea; as a method of treatment for preterm birth, when said animal has a shortened cervix, and other disease states or conditions treated with supplemental progesterone (collectively, "Progesterone-deficient States"); and the use of formulations as described herein wherein estradiol is at least one API in said formulation for the treatment of an animal, including humans, having menopause-related symptoms including, for example, vasomotor symptoms; in relation to treatment of hypoestrogenism related symptoms including, for example and without limitation, hot flashes and night sweats (vasomotor symptoms), sleep disturbances, mood changes and vulvo-vaginal atrophy; and osteoporosis and other non-menopausal disease states or conditions treated with supplemental estrogen. (collectively, "Estrogen-deficient States"), each in a subject in need of treatment, and each with a non-toxic effective amount of said formulations. As used herein, the term "treatment", or a derivative thereof, contemplates partial or complete inhibition of the stated disease state when a formulation as described herein is administered prophylactically or following the onset of the disease state for which such formulation is administered. For the purposes of the present disclosure, "prophylaxis" refers to administration of the active ingredient(s) to an animal to protect the animal from any of the disorders set forth herein, as well as others.

Unless otherwise specified, "natural," as used herein with reference to hormones discussed herein, means bio-identical hormones formulated to match the chemical structure and effect of those that occur naturally in the human body (endogenous). An exemplary natural estrogen is estradiol (also described as 17β-estradiol and E2) and a natural progestin is progesterone. An exemplary cyclic/sequential regimen comprises delivery of from about 0.125 mg to about 2.0 mg of estradiol daily for 14-18 days, followed by delivery of from about 0.125 mg to about 2 mg of estradiol and about 25 mg to about 200 mg of progesterone daily for 10-14 days. Cyclic/sequential regimens may be especially useful for menopausal females. Other exemplary dosage strengths for estradiol for use in the formulations described herein include, without limitation, 0.125, 0.25, 0.375, 0.50, 0.625, 0.75, 1.00, 1.125, 1.25, 1.375, 1.50, 1.625, 1.75 and 2.00 mg. Other exemplary dosage strengths for progesterone for use in the formulations described herein include, without limitation, 25, 50, 75, 100, 125, 150, 175, 200 mg, 250 mg, 300 mg, 350 mg and 400 mg. These dosage strengths for each of estradiol and progesterone can be administered in formulations described herein either alone or in combination.

Progesterone active pharmaceutical ingredient may be micronized via any one of the multiple methods typically utilized by the ordinarily skilled artisan. In various embodiments, micronized progesterone has an X50 particle size value of less than about 15 microns, less than about 10 microns, less than about 5 microns and/or less than about 3 microns. In various embodiments, micronized progesterone has an X90 particle size value of less than about 25 microns, less than about 20 microns, and/or less than about 15 microns.

Particle size may be determined in any suitable manner. For example, a Beckman Coulter LS 13 320 Laser Diffraction Particle Size Analyzer (the "Beckman Device") may be used to determine particle size. As described above, particle size may be represented by various metrics, for example, through an X50 particle size, and/or X90 particle size, or similar descriptions of particle size.

The Beckman Device may be used with various modules for introducing a sample for analysis. The Beckman Device may be used with the LS 13 320 Universal Liquid Module ("ULM"). The ULM is capable of suspending samples in the size range of 0.017 µm to 2000 µm. The ULM is a liquid based module that allows for delivery of the sample to the sensing zone. The ULM recirculates the sample through the Beckman Device. The ULM comprises two hoses, one for fluid delivery and another for waste. The total volume used may be 125 mL or less. A sample mass of from about 1 mg to about 10 g may be used. The ULM may interact with the Beckman Device via pins that fit into slots on the ULM. The ULM may use a variety of suspension fluids, for example, water, butonol, ethanol, chloroform, heptanes, toluene, propanol, COULTER Type 1B Dispersant ("Coulter 1B"), and a variety of other suspension fluids. Surfactants may also be used, though pump speed should be adjusted to prevent excessive bubbling. Coulter 1B may comprise one or more of acetaldehyde, ethylene oxide, and/or 1,4-dioxane. The Beckman Device may be configured to use a variety of optical theories, including the Fraunhofer optical model and the Mie Theory.

The Beckman Device may comprise software to control the Beckman Device while the ULM is in use. The software may control, for example, pump speed, use of de-bubble routine, rinse routine, sonicate routine, and fill routine, among others. Parameters regarding the sample run may also be configured. For example, run length may be set. Though any suitable run length may be used, in various embodiments, a time period of 30 seconds to 120 seconds, and preferably between 30 seconds and 90 seconds may be used.

The Beckman Device may be used with the LS 13 320 Micro Liquid Module ("MLM"). The MLM is capable of suspending samples in the size range of 0.4 µm to 2000 µm. The MLM is a liquid based module that allows for delivery of the sample to the sensing zone. The MLM includes a stirrer. The total volume used may be 12 mL or less. The MLM may use a variety of suspension fluids, both aqueous and non-aqueous.

Each of estradiol and progesterone as described herein can be formulated alone pursuant to the teachings below. These formulations can be prepared for oral administration or can be combined, based on compatibility, for co-administration of estradiol and progesterone in a single oral unit dosage form.

Progesterone formulations of the present disclosure are prepared via blending with a pharmaceutically acceptable oil;

generally, the oil comprises at least one medium chain fatty acid such as medium chain fatty acids consisting of at least one mono-, di-, or triglyceride, or derivatives thereof, or combinations thereof. Optionally added are other excipients including, for example and without limitation, anti-oxidants, lubricants and the like. Sufficient oil is used to form a suspension of micronized progesterone or, in the alternative, solubilize progesterone.

Pharmaceutically acceptable oils include, without limitation, the use of at least one of a caproic fatty acid; a caprylic fatty acid; a capric fatty acid; a tauric acid; a myristic acid; a linoleic acid; a succinic acid; a glycerin; mono-, di-, or triglycerides and combinations and derivatives thereof; a polyethylene glycol; a polyethylene glycol glyceride (GELUCIRE (a polyethylene glycol glyceride); GATTEFOSSE SAS, Saint-Priest, France); a propylene glycol; a caprylic/capric triglyceride (MIGLYOL (caprylic/capric triglyceride); SASOL Germany GMBH, Hamburg; MIGLYOL (caprylic/capric triglyceride) includes MIGLYOL 810 (Caprylic/Capric Triglyceride), MIGLYOL 812 (Caprylic/Capric Triglyceride), MIGLYOL 816 (Caprylic/Capric Triglyceride) and MIGLYOL 829 (Caprylic/Capric/Succinic Triglyceride); a caproic/caprylic/capric/lauric triglyceride; a caprylic/capric/linoleic triglyceride; a caprylic/capric/succinic triglyceride; a propylene glycol monocaprylate; propylene glycol monocaprate; (CAPMUL PG-8 (Propylene Glycol Monocaprylate) and CAPMUL PG-10 (Propylene Glycol Monocaprate); the CAPMUL brands are owned by ABITEC, Columbus Ohio); a propylene glycol dicaprylate; a propylene glycol dicaprylate; medium chain mono- and di-glycerides (CAPMUL MCM (Medium Chain Mono- and Diglycerides)); a diethylene glycol mono ester (including 2-(2-Ethoxyethoxy)ethanol: TRANSCUTOL (diethylene glycol mono ester)); a diethylene glycol monoethyl; esters of saturated coconut and palm kernel oil and derivatives thereof; triglycerides of fractionated vegetable fatty acids, and combinations and derivatives thereof.

In other aspects and embodiments, progesterone is fully solubilized using, for example and without limitation, sufficient amounts of: TRANSCUTOL (Diethylene glycol monoethyl ether) and MIGLYOL (caprylic/capric triglyceride); TRANSCUTOL (Diethylene glycol monoethyl ether), MIGLYOL (caprylic/capric triglyceride) and CAPMUL PG-8 (Propylene Glycol Monocaprylate) and/or CAPMUL PG-10 (Propylene Glycol Monocaprate); CAPMUL MCM (Medium Chain Mono- and Diglycerides); CAPMUL MCM (Medium Chain Mono- and Diglycerides) and a non-ionic surfactant; and CAPMUL MCM (Medium Chain Mono- and Diglycerides) and GELUCIRE (a polyethylene glycol glyceride).

Various ratios of these oils can be used for full solubilization of progesterone. CAPMUL MCM (Medium Chain Mono- and Diglycerides) and a non-ionic surfactant can be used at ratios including, for example and without limitation: 65:35, 70:30, 75:25, 80:20, 85:15 and 90:10. CAPMUL MCM (Medium Chain Mono- and Diglycerides) and GELUCIRE (a polyethylene glycol glyceride) can be used at ratios including, for example and without limitation, 6:4, 7:3, 8:2, and 9:1. Among other combinations, these oils and/or solubilizers, as defined herein, and combinations thereof, can be used to form combination estradiol and progesterone formulations of the present disclosure.

Combinations of these oils can produce partially solubilized progesterone, depending upon the desired unit dosage amount of progesterone. The greater the amount of progesterone per unit dosage form, the less progesterone may be solubilized. The upward limit of dosage strength per unit dose it generally limited only by the practical size of the final dosage form.

In various embodiments, estradiol is partially, substantially or completely solubilized. Solubilized estradiol may include estradiol that is approximately: 90% soluble in a solvent; 93% soluble in a solvent; 95% soluble in a solvent; 97% soluble in a solvent; 99% soluble in a solvent; and 100% soluble in a solvent. Solubility may be expressed as a mass fraction (% w/w).

In various embodiments, the solubilizing agent is selected from at least one of a solvent or co-solvent. Suitable solvents and co-solvents include any mono-, di- or triglyceride and glycols, and combinations thereof.

In addition to the oils referenced above for progesterone, which can also be used as solubilizers for estradiol, other solubilizers include, for example and without limitation, glyceryl mono- and di-caprylates, propylene glycol and 1,2,3-propanetriol (glycerol, glycerin, glycerine).

Anionic and/or non-ionic surfactants can be used in other embodiments of the presently disclosed formulations containing estradiol, progesterone or a combination thereof. In certain embodiments, a non-ionic surfactant is used. Exemplary non-ionic surfactants may include, for example and without limitation, one or more of oleic acid, linoleic acid, palmitic acid, and stearic acid. In further embodiments, the non-ionic surfactant may comprise polyethylene sorbitol esters, including polysorbate 80, which is commercially available under the trademark TWEEN 80® (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and in certain embodiments, about 30% of the formulation total mass.

In various other embodiments, the non-ionic surfactant is selected from one or more of glycerol and polyethylene glycol esters of long chain fatty acids, for example, lauroyl macrogol-32 glycerides and/or lauroyl polyoxyl-32 glycerides, commercially available as Gelucire, including, for example, Gelucire 44/11 and Gelucire 44/14. These surfactants may be used at concentrations greater than about 0.01%, and typically in various amounts of about 0.01%-10.0%, 10.1%-20%, and 20.1%-30%.

In other embodiments, a lubricant is used. Any suitable lubricant may be used, such as for example lecithin. Lecithin may comprise a mixture of phospholipids.

In additional embodiments, an antioxidant is used. Any suitable anti-oxidant may be used such as, for example and without limitation butylated hydroxytoluene.

For example, in various embodiments, a pharmaceutical formulation comprises about 20% to about 80% carrier by weight, about 0.1% to about 5% lubricant by weight, and about 0.01% to about 0.1% antioxidant by weight.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

As is with all oils, solubilizers, excipients and any other additives used in the formulations described herein, each is to be non-toxic and pharmaceutically acceptable.

As referenced above, the formulations of the present disclosure are generally orally administered, typically via, for example, capsules such as soft capsules. The present formulations can also be used to form transdermal patches using standard technology known in the art. Solubilized formulations of the present invention can also be formulated for intraperitoneal administration using techniques well known in the art.

In accordance with various embodiments, formulations do not include peanut oil. The lack of peanut oil obviates the risk posed to those having peanut-based allergies.

According to various embodiments described herein, a 28-day or monthly regimen of capsules can be packaged in a single kit (e.g., a blister pack) having administration days identified to improve compliance and reduce associated symptoms, among others. One or more of the capsules may contain no estradiol, for example, and/or no progesterone. Capsules that comprise no estrogen or progesterone API may be referred to as placebos. A blister pack can have a plurality of scores or perforations separating blister pack into 28 days. Each day may further comprise a single blister or a plurality of blisters. In various embodiments, each unit dose may contain micronized and/or partially solubilized, or fully solubilized progesterone and/or solubilized estradiol in amounts as set forth herein above, although other dose ranges may be contemplated. In addition, kits having other configurations are also contemplated herein. For example, without limitation, kits having such blister packs may contain any number of capsules.

Orally administered formulations of the present disclosure containing micronized and/or partially solubilized, or fully solubilized, progesterone are also used for the treatment of endometrial hyperplasia, secondary amenorrhea and other disease states treated with supplemental progesterone. Generally, progesterone-containing formulations described herein are used to treat the effects of the administration of supplemental estrogen whether administered alone or in combination with solubilized estradiol of the present disclosure or other estrogen-containing formulations. In various other embodiments, a capsule containing formulations of the present disclosure, for example a softgel capsule, may be applied in or around the vagina.

Formulations of the present disclosure containing solubilized estradiol are used to treat Estrogen-deficient States, including vasomotor symptoms, for example, in relation to treatment of hypoestrogenism related symptoms including, for example and without limitation, hot flashes and night sweats (vasomotor symptoms), sleep disturbances, mood changes, vulvo-vaginal atrophy, and osteoporosis and other non-menopausal disease states treated with supplemental estrogen.

Formulations of the present disclosure containing solubilized estradiol may be used to treat or prevent atrophic vaginitis or vulvo-vaginal atrophy. In various embodiments, a capsule, for example a softgel capsule, may be applied in or around the vagina.

Additional objects of the present disclosure includes: providing increased patient compliance secondary to ease of use; providing increased physician adoption secondary to ease of use/instruction with less worry of side effects from inappropriate usage; providing decreased side-effects from erroneous use (decreased irregular bleeding); providing better efficacy/control of symptoms secondary to appropriate use; reducing the metabolic and vascular side effects of the commonly used synthetic progestins when administered alone or in combination with an estrogen (norethindrone acetate, medroxyprogesterone acetate, etc.) including, for example, stroke, heart attacks, blood clots and breast cancer.

EXAMPLES

Example 1

Estradiol Solubility

In various experiments, suitable solvents were determined for providing sufficient solubility to make 2 mg of estradiol in a 100 mg fill mass, with a desired goal of achieving ~20 mg/g solubility for estradiol. Initial solubility experiments were done by mixing estradiol with various solvents, saturate the solution with the estradiol, equilibrate for at least 3 days and filter the un-dissolved particles and analyzing the clear supernatant for the amount of estradiol dissolved by HPLC.

Estradiol solubility experiments were performed. From this list at least one item (e.g. propylene glycol) is known to be unsuitable for encapsulation.

TABLE 1

| Ingredient | Solubility (mg/g) |
| --- | --- |
| PEG 400 | 105* |
| Propylene Glycol | 75* |
| Polysorbate 80 | 36* |
| TRANSCUTOL HP (Highly purified diethylene glycol monoethyl ether EP/NF) | 141 |
| CAPMUL PG-8 (Propylene Glycol Monocaprylate) | 31.2 |

*Literature reference - Salole, E. G. (1987) The Physicochemical Properties of Oestradiol, J Pharm and Biomed Analysis, 5, 635-640.

Example 2

It was desired to achieve 50 mg of progesterone suspended in a medium that can also solubilize 2 mg estradiol in a total capsule fill mass of 200 mg. In order to achieve this formulation, the required solubility of estradiol needs to be ~10 mg/g. A total fill weight of 200 mg was considered suitable for a size 5 oval soft gelatin capsule.

Additional solubility studies were performed to find solvent mixtures that might possibly be more suitable for soft gelatin encapsulation. Solubility studies were conducted with CAPMUL PG-8 (Propylene Glycol Monocaprylate) and CAPMUL MCM (Medium Chain Mono- and Diglycerides) by mixing estradiol with various the solvent systems and as before by analyzing for the amount of estradiol dissolved by HPLC after filtration. Results of these experiments are presented in Table 2. It can be seen from these results that mixtures containing MIGLYOL (caprylic/capric triglyceride):CAPMUL PG-8 (Propylene Glycol Monocaprylate) at 50%; and also CAPMUL MCM (Medium Chain Mono- and Diglycerides) alone or in combination with 20% Polysorbate 80 can achieve sufficient solubility to meet the target of 10 mg/g. CAPMUL PG-8 (Propylene Glycol Monocaprylate) mixed with MIGLYOL (caprylic/capric triglyceride) at the 15 and 30% level did not provide sufficient solubility.

TABLE 2

| Ingredient | Solubility (mg/g) |
| --- | --- |
| MIGLYOL (caprylic/capric triglyceride):CAPMUL PG-8 (Propylene Glycol Monocaprylate) (85:15) | 4.40 |

TABLE 2-continued

| Ingredient | Solubility (mg/g) |
|---|---|
| MIGLYOL (caprylic/capric triglyceride):CAPMUL PG-8 (Propylene Glycol Monocaprylate) (70:30) | 8.60 |
| TRANSCUTOL (Diethylene glycol monoethyl ether):MIGLYOL 812 (Caprylic/Capric Triglyceride):CAPMUL PG-8 (Propylene Glycol Monocaprylate) (5:65:28) | >12 |
| TRANSCUTOL (Diethylene glycol monoethyl ether):MIGLYOL 812 (Caprylic/Capric Triglyceride):CAPMUL PG-8 (Propylene Glycol Monocaprylate) (5:47:47) | >12 |
| MIGLYOL (caprylic/capric triglyceride):CAPMUL PG-8 (Propylene Glycol Monocaprylate) (50:50) | 14.0 |
| CAPMUL MCM (Medium Chain Mono- and Diglycerides) | 19.8 |
| Polysorbate 80:CAPMUL MCM (Medium Chain Mono- and Diglycerides) (20:80) | 15.0 |

Example 3

Additional studies were performed to assess the stability of estradiol (4-6 mg) in solvent mixtures, as reported in Table 3. MIGLYOL 812 (Caprylic/Capric Triglyceride) with 4% TRANSCUTOL (Diethylene glycol monoethyl ether) precipitated on Hot/Cold cycling after 96 hours, while estradiol solubilized in MIGLYOL (caprylic/capric triglyceride):CAPMUL (a propylene glycol monocaprylate; propylene glycol monocaprate) blends at 30 and 50% or in CAPMUL MCM (Medium Chain Mono- and Diglycerides) alone, did not precipitate under the same conditions for a minimum of 14 days.

TABLE 3

| Formulation | Estradiol mg/g | Results Hot/Cold Cycling |
|---|---|---|
| TRANSCUTOL (Diethylene glycol monoethyl ether):MIGLYOL 812 (Caprylic/Capric Triglyceride) (4:96) | 4 | Crystallizes after 96 hours |
| MIGLYOL 812 (Caprylic/Capric Triglyceride):CAPMUL PG-8 (Propylene Glycol Monocaprylate) (70:30) | 6 | Clear, after 14 days |
| MIGLYOL 812 (Caprylic/Capric Triglyceride):CAPMUL PG-8 (Propylene Glycol Monocaprylate) (50:50) | 6 | Clear, after 14 days |
| TRANSCUTOL (Diethylene glycol monoethyl ether):MIGLYOL 812 (Caprylic/Capric Triglyceride):CAPMUL PG-8 (Propylene Glycol Monocaprylate) (5:80:15) | 6 | Clear, after 14 days |
| CAPMUL MCM (Medium Chain Mono- and Diglycerides) | 6 | Clear after 14 days |

12 mg estradiol solubilized in MIGLYOL (caprylic/capric triglyceride):CAPMUL PG-8 (Propylene Glycol Monocaprylate) 50:50, CAPMUL MCM (Medium Chain Mono- and Diglycerides), and in mixtures of TRANSCUTOL (Diethylene glycol monoethyl ether): MIGLYOL (caprylic/capric triglyceride):CAPMUL PG-8 (Propylene Glycol Monocaprylate) are stable and do not precipitate for at least 12 days.

TABLE 4

| Formulation | Estradiol mg/g | Results Hot/Cold Cycling |
|---|---|---|
| MIGLYOL 812 (Caprylic/Capric Triglyceride):CAPMUL PG-8 (Propylene Glycol Monocaprylate) (50:50) | 12 | Clear, after 12 days |
| TRANSCUTOL (Diethylene glycol monoethyl ether):MIGLYOL 812 (Caprylic/Capric Triglyceride):CAPMUL PG-8 (Propylene Glycol Monocaprylate) (5:65:28) | 12 | Clear, after 12 days |
| TRANSCUTOL (Diethylene glycol monoethyl ether):MIGLYOL 812 (Caprylic/Capric Triglyceride):CAPMUL PG-8 (Propylene Glycol Monocaprylate) (5:47:47) | 12 | Clear, after 12 days |
| CAPMUL MCM (Medium Chain Mono- and Diglycerides) | 12 | Clear after 12 days |

Example 4

In addition to determining physical stability of the estradiol solutions over time, it is necessary to determine if the fill material will be stable during the encapsulation process. One way to test these preparations is with the addition of water to the fill mass. As can be seen in Table 5, estradiol solutions at a concentration of 6 mg/g in Polyethylene Glycol 400 and CAPMUL MCM (Medium Chain Mono- and Diglycerides) are able to absorb a minimum of 7% water without recrystallization, whereas the same concentration in MIGLYOL 812 (Caprylic/Capric Triglyceride):CAPMUL PG-8 (Propylene Glycol Monocaprylate) (75:25) precipitates.

Estradiol solutions at a concentration of 12 mg/g in Polyethylene Glycol 400 and CAPMUL MCM (Medium Chain Mono- and Diglycerides) are able to absorb a minimum of 7% water without recrystallization. All CAPMUL PG-8 (Propylene Glycol Monocaprylate) containing formulations turned hazy on the addition of water. However, it should be noted that estradiol recrystallization was not observed, and the addition of water to CAPMUL PG-8 (Propylene Glycol Monocaprylate) alone (without any estradiol) also turns hazy on the addition of water.

TABLE 5

| Formulation | Estradiol mg/g | Results after addition of 7% water |
|---|---|---|
| MIGLYOL 812 (Caprylic/Capric Triglyceride):CAPMUL PG-8 (Propylene Glycol Monocaprylate) (75:25) | 6 | Precipitated |
| MIGLYOL 812 (Caprylic/Capric Triglyceride):CAPMUL PG-8 (Propylene Glycol Monocaprylate) (50:50) | 12 | Hazy |

TABLE 5-continued

| Formulation | Estradiol mg/g | Results after addition of 7% water |
|---|---|---|
| TRANSCUTOL (Diethylene glycol monoethyl ether):MIGLYOL 812 (Caprylic/Capric Triglyceride):CAPMUL PG-8 (Propylene Glycol Monocaprylate) (5:65:28) | 12 | Hazy |
| CAPMUL MCM (Medium Chain Mono- and Diglycerides) | 12 | Clear |
| TRANSCUTOL (Diethylene glycol monoethyl ether):MIGLYOL 812 (Caprylic/Capric Triglyceride):CAPMUL PG-8 (Propylene Glycol Monocaprylate) (5:47:47) | 12 | Hazy |
| Polyethylene Glycol 400 | 12 | clear |

Example 5

In an exemplary embodiment, a capsule is provided containing a fill material comprising:

TABLE 6

| Ingredient | Mg/Capsule |
|---|---|
| Estradiol Hemihydrate | 2.00 |
| Mono-, di- or triglyceride (Miglyol 812) | qs |
| Diethylene Glycol Monoethylether (TRANSCUTOL HP (Highly purified diethylene glycol monoethyl ether EP/NF)) | 65.00 |
| Liquid lecithin | 1.63 |
| Butylated Hydroxytoluene | 0.13 |
| Total Fill Weight | 325 |

Example 6

In an exemplary embodiment, a capsule is provided containing a fill material comprising:

TABLE 7

| Ingredient | Mg/Capsule |
|---|---|
| Estradiol Hemihydrate | 2.00 |
| Monoglycerides/diglycerides/triglycerides of caprylic/capric acid (CAPMUL MCM (Medium Chain Mono- and Diglycerides)) | qs |
| Liquid lecithin | 1.63 |
| Polysorbate 80 | 97.5 |
| Total Fill Weight | 325 |

In an exemplary embodiment, a capsule is provided containing a fill material comprising:

TABLE 8

| Ingredient | Mg/Capsule | % w/w | Amount/Batch |
|---|---|---|---|
| Estradiol Hemihydrate | 2.03 | 0.62 | 20.2 g |
| Monoglycerides/diglycerides/triglycerides of caprylic/capric acid (CAPMUL MCM (Medium Chain Mono- and Diglycerides)) | 322.97 | 99.38 | 3.23 kg |
| Total | | 100 | 3.25 kg |

The above formulation is prepared as follows: estradiol is added to CAPMUL MCM (Medium Chain Mono- and Diglycerides) and mixed until dissolved.

Example 7

Progesterone Solubility

In various embodiments, both estradiol and progesterone may be dissolved in a solvent. In various embodiments, the solubility of both estradiol and progesterone will be such that a therapeutically effective dose may be obtained in a reasonably sized mass, generally considered to be between 1 mg and 1200 mg, preferably suitable for encapsulation in a size 3 to 22 oval or oblong capsule. For example, in various embodiments, 50 mg to 100 mg of progesterone may be dissolved in a volume of solvent; i.e., the solubility would be 50 mg to 100 mg per capsule. MIGLYOL (caprylic/capric triglyceride) was attempted, and while it can be considered a good carrier for progesterone, it alone did not provide a desirable level of solubilization of estradiol (e.g., solubility of 12 mg/g may be desirable in various embodiments). Thus, MIGLYOL (caprylic/capric triglyceride) may be used in embodiments comprising a suspension of progesterone, though MIGLYOL (caprylic/capric triglyceride), standing alone, is not desirable for use in embodiments having fully solubilized progesterone and/or estradiol.

As can be seen in Table 9, the solubility of progesterone in CAPMUL MCM (Medium Chain Mono- and Diglycerides) is ~73 mg/g. Therefore, by suspending 200 mg progesterone in 400 mg of solvent, part of the dose (~14%) is already dissolved and the remaining is still a suspension. In some aspects and embodiments, it is desired to minimize the partial solubility of progesterone in the formulation in order to minimize the possibility of recrystallization.

Based on 73 mg/g solubility, the capsule size required to make a capsule of 50 mg solubilized progesterone would be 685 mg. Therefore, it was shown that it would be feasible to make a 50 mg progesterone and 2 mg estradiol solubilized formulation. MIGLYOL (caprylic/capric triglyceride) had the lowest solubility, but that solvent is unable to dissolve the estradiol, therefore under further experiments, it was decided to proceed with the second lowest or CAPMUL MCM (Medium Chain Mono- and Diglycerides). It has also been found that 2 mg of estradiol may also be dissolved in 685 mg of CAPMUL MCM (Medium Chain Mono- and Diglycerides).

TABLE 9

| Ingredient | Progesterone Solubility (mg/g) |
|---|---|
| CAPMUL MCM (Medium Chain Mono- and Diglycerides) | 73.4 |
| CAPMUL PG-8 (Propylene Glycol Monocaprylate) | 95 |
| MIGLYOL 812 (Caprylic/Capric Triglyceride) | 27.8 |

In addition, it has been found that the solubility of progesterone in a solvent of CAPMUL MCM (Medium Chain Mono- and Diglycerides) in combination with Gelucire 44/14 in a 9:1 ratio increases the solubility to approximately 86 mg/g. Therefore, in various embodiments, progesterone and/or estradiol may be dissolved in a CAPMUL MCM (Medium Chain Mono- and Diglycerides) and Gelucire 44/14 system, wherein the ratio of CAPMUL MCM (Medium Chain Mono- and Diglycerides) to GELUCIRE 44/14 (Lauroyl macrogol- 32 glycerides EP Lauroyl polyoxyl-32 glycerides NF Lauroyl polyoxylglycerides (USA FDA IIG)) is 9:1.

TABLE 10

| Ingredient | Progesterone Solubility (mg/g) |
|---|---|
| CAPMUL MCM (Medium Chain Mono- and Diglycerides):GELUCIRE 44/14 (Lauroyl macrogol-32 glycerides EP Lauroyl polyoxyl-32 glycerides NF Lauroyl polyoxylglycerides (USA FDA IIG)) (9:1) | 86.4 |
| CAPMUL MCM (Medium Chain Mono- and Diglycerides) GELUCIRE 44/14 (Lauroyl macrogol-32 glycerides EP Lauroyl polyoxyl-32 glycerides NF Lauroyl polyoxylglycerides (USA FDA IIG)) (7:3) | 70.5 |
| CAPMUL MCM (Medium Chain Mono- and Diglycerides):GELUCIRE 44/14 (Lauroyl macrogol-32 glycerides EP Lauroyl polyoxyl-32 glycerides NF Lauroyl polyoxylglycerides (USA FDA IIG)) (6:4) | 57.4 |

Example 7

In an exemplary embodiment, a capsule is provided containing a fill material having fully solubilized progesterone and estradiol comprising:

TABLE 11

| Ingredient | Mass (mg) | % w/w | Qty/Capsule (mg) |
|---|---|---|---|
| Progesterone, USP, micronized | 50.00 | 7.14 | 50.00 |
| Estradiol Hemihydrate, USP | 2.03 | 0.29 | 2.03 |
| CAPMUL MCM (Medium Chain Mono- and Diglycerides), NF | | 82.57 | 577.97 |
| GELUCIRE 44/14 (Lauroyl macrogol-32 glycerides EP Lauroyl polyoxyl-32 glycerides NF Lauroyl polyoxylglycerides (USA FDA IIG)), NF | | 10.0 | 70.00 |
| TOTAL | | 100.00 | 700.00 |

A capsule such as that shown in TABLE 11 may be manufactured in any suitable manner. For the purposes of this Example, mixing may be facilitated by an impellor, agitator, or other suitable means. Also for the purposes of this Example, heating and/or mixing may be performed under an inert or relatively inert gas atmosphere, such as nitrogen gas $N_2$. Mixing and/or heating for the purposes of this Example may be performed in any suitable vessel, such as a stainless steel vessel.

For example, CAPMUL MCM (Medium Chain Mono- and Diglycerides) may be heated to between 30° C. to 50° C., more preferably from 35° C. to 45° C., and more preferably to 40° C.+/−2° C. GELUCIRE 44/14 (Lauroyl macrogol-32 glycerides EP Lauroyl polyoxyl-32 glycerides NF Lauroyl polyoxylglycerides (USA FDA IIG)) may be added to the CAPMUL MCM (Medium Chain Mono- and Diglycerides) and mixed until dissolved. The addition may occur all at once or may occur gradually over a period of time. Heat may continue to be applied during the mixing of the Gelucire 44/14 and the CAPMUL MCM (Medium Chain Mono- and Diglycerides).

Heat may be removed from the GELUCIRE 44/14 (Lauroyl macrogol-32 glycerides EP Lauroyl polyoxyl-32 glycerides NF Lauroyl polyoxylglycerides (USA FDA IIG)) and CAPMUL MCM (Medium Chain Mono- and Diglycerides) mixture. Estradiol Hemihydrate may be added to the mixture. The addition may occur all at once or may occur gradually over a period of time. Micronized progesterone may then be added to the Gelucire 44/14, CAPMUL MCM (Medium Chain Mono- and Diglycerides) and Estradiol Hemihydrate mixture until dissolved. The addition may occur all at once or may occur gradually over a period of time.

Example 8

In an exemplary embodiment, a capsule is provided containing a fill material having suspended progesterone comprising:

TABLE 12

| Ingredient | mg/Capsule | % | Function |
|---|---|---|---|
| Micronized Progesterone | 200.00 | 30.77 | Active |
| Medium Chain Triglyceride (MIGLYOL 812 (Caprylic/Capric Triglyceride) or equivalent) | qs | qs | Carrier |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL (caprylic/capric triglyceride) is heated to about 45° C. GELUCIRE 44/14 (Lauroyl macrogol-32 glycerides EP Lauroyl polyoxyl-32 glycerides NF Lauroyl polyoxylglycerides (USA FDA IIG)) is added and mixed until dissolved. BHT is added and mixed until dissolved. Progesterone is suspended and passed through a colloid mill. The resultant fill mass can be used for encapsulation.

In an exemplary embodiment, a capsule is provided containing a fill material having partially solubilized progesterone comprising:

TABLE 13

| Ingredient | Qty/Capsule (mg) | % w/w | Qty/Capsule (mg) | Amount/Batch (kg) |
|---|---|---|---|---|
| Micronized Progesterone, USP | 200.00 | 33.33 | Active | 2.0 |
| Monoglycerides/diglycerides/triglycerides of caprylic/capric acid (CAPMUL MCM (Medium Chain Mono- and Diglycerides)) | 394.0 | 65.67 | Carrier | 3.94 |
| Lauroyl polyoxyl-32-glycerides (GELUCIRE 44/14 (Lauroyl macrogol-32 glycerides EP Lauroyl polyoxyl-32 glycerides NF Lauroyl polyoxylglycerides (USA FDA IIG)) or equivalent) | 6.0 | 1 | Lubricant/Emulsifier | 0.06 |
| Total | 600.00 mg | 100 | | 6.0 kg |

For suspensions of progesterone and partially solubilized progesterone, GELUCIRE 44/14 may be added at 1% to 2% w/w to increase viscosity. The above formulation is prepared as follows: CAPMUL MCM (Medium Chain Mono- and Diglycerides) is heated to about 65° C. GELUCIRE 44/14 (Lauroyl macrogol-32 glycerides EP Lauroyl polyoxyl-32 glycerides NF Lauroyl polyoxylglycerides (USA FDA IIG)) is added and mixed until dissolved. Heat is removed. Progesterone is added and the mixture is passed through a colloid mill. The resultant fill mass can be used for encapsulation.

Example 9

In an exemplary embodiment, a capsule is provided containing a fill material having suspended progesterone comprising:

TABLE 14

| Ingredient | % | mg/Capsule | Function |
|---|---|---|---|
| Micronized Progesterone | 30.77 | 200.00 | Active |
| Medium Chain Triglyceride (MIGLYOL 812 (Caprylic/Capric Triglyceride) or equivalent) | 65.93 | 428.55 | Carrier |
| Lauroyl polyoxyl-32-glycerides (GELUCIRE 44/14 (Lauroyl macrogol-32 glycerides EP Lauroyl polyoxyl-32 glycerides NF Lauroyl polyoxylglycerides (USA FDA IIG)) or equivalent) | 3.00 | 19.50 | Suspending Agent |
| Butylated Hydroxytoluene | 0.03 | 1.95 | Antioxidant |
| Total | 100 | 650 | |

In various embodiments, amounts of MIGLYOL (caprylic/capric triglyceride) may be present in a range from about 35-95% by weight; GELUCIRE 44/14 (Lauroyl macrogol-32 glycerides EP Lauroyl polyoxyl-32 glycerides NF Lauroyl polyoxylglycerides (USA FDA IIG)) from about 0.5-30% by weight; and BHT from about 0.01-0.1% by weight.

Example 10

For the purposes of this Example, a particle size analysis is conducted by using the Beckman Device. A sample API comprising micronized progesterone in accordance with various embodiments is provided for analysis.

Figure 4:
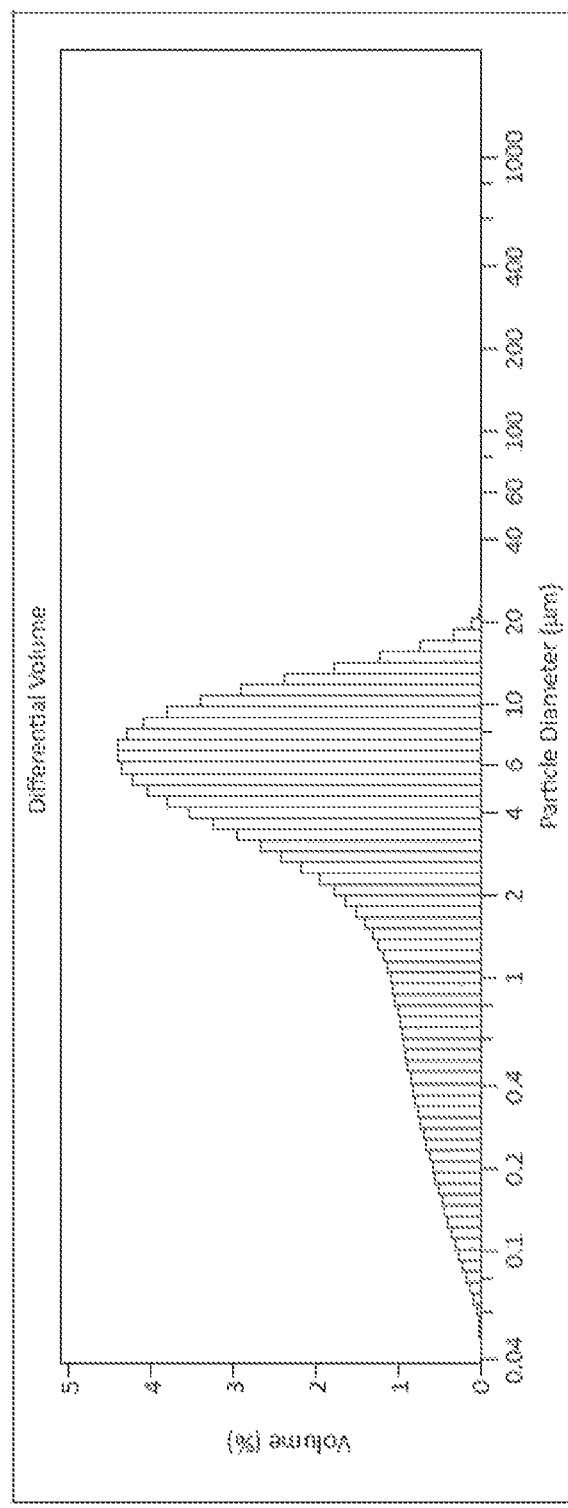
FIG. 4 illustrates a graph of the particle distribution obtained in Example 10.

Approximately 0.01 g of a sample API in accordance with various embodiments was combined with Coulter 1B and 10 mL of deionized water. Sonication was performed for 15 seconds. The Beckman Device, equipped with a ULM, performed analysis for 90 seconds. The Beckman Device was configured to use the Fraunhofer optical model. The Beckman Device yielded that the sample has an X50 of 4.279 µm, an X75 of 7.442 µm, and an X25 of 1.590 µm. The Beckman Device also yielded that the mean particle size is 4.975 µm, the median particle size is 4.279 µm, the mode particle size is 6.453 µm, and the standard deviation is 3.956 µm. A graph of the particle distribution obtained is shown in FIG. 4.

Example 11

A formulation sample having approximately 200 mg of micronized progesterone and 2 mg of estradiol was dispersed with oil. The Beckman Device, equipped with a MLM, performed analysis for 60 seconds. The Beckman Device was configured to use the Fraunhofer optical model. The Beckman Device yielded that the sample has an X50 of 11.0 µm, an X75 of 17.3 µm, and an X25 of 5.3 µm. The Beckman Device also yielded that the mean particle size is 11.8 µm, the median particle size is 11.04 µm, the mode particle size is 13.6 µm, and the standard deviation is 7.8 µm.

Example 12

In order to increase the solubility of progesterone in the final solution, GELUCIRE 44/14 (Lauroyl macrogol-32 glycerides EP Lauroyl polyoxyl-32 glycerides NF Lauroyl polyoxylglycerides (USA FDA IIG)) was added at about 10% w/w.

TABLE 15

Quantitative Formula: Batch Size 10,000 capsules

| Item No. | Ingredient(s) | Label Claim (mg) | % w/w | Qty/Capsule (mg) | Amount/Batch (kg) |
|---|---|---|---|---|---|
| 1. | Progesterone, USP, micronized | 50.00 | 7.14 | 50.00 | 0.50 |
| 2. | Estradiol Hemihydrate, USP | 2.03 | 0.29 | 2.03 | 0.02 |
| 3. | CAPMUL MCM (Medium Chain Mono- and Diglycerides), NF | | 82.57 | 577.97 | 5.78 |
| 4. | GELUCIRE 44/14 (Lauroyl macrogol-32 glycerides EP Lauroyl polyoxyl-32 glycerides NF Lauroyl polyoxylglycerides (USA FDA IIG)) Gelucire 44/14, NF | | 10.0 | 70.00 | 0.70 |
| | Total: | | 100.00 | 700.00 | 7.00 |

An example of the final formulation is provided in Table 15. The manufacturing process is as follows. CAPMUL MCM (Medium Chain Mono- and Diglycerides) is heated to 40° C. GELUCIRE 44/14 (Lauroyl macrogol-32 glycerides EP Lauroyl polyoxyl-32 glycerides NF Lauroyl polyoxylglycerides (USA FDA IIG)) is added and mixed until dissolved. Heat is removed. Estradiol is added and mixed until dissolved. Micronized progesterone is then added and mixed until dissolved.

Example 13

In an exemplary embodiment, a capsule is provided containing a fill material having fully solubilized estradiol and partially solubilized progesterone comprising:

TABLE 16

| Item No. | Ingredient(s) | Label Claim (mg) | % w/w | Qty/Capsule (mg) | Amount/Batch (g) |
|---|---|---|---|---|---|
| 1. | Progesterone, USP, micronized | 50.00 | 25.000 | 50.00 | 500.00 |
| 2. | Estradiol Hemihydrate | 0.25 | 0.129 | 0.26 | 2.58 |
| 3. | CAPMUL MCM (Medium Chain Mono- and Diglycerides), NF | | 73.371 | 146.74 | 1467.42 |
| 4. | GELUCIRE 44/14 (Lauroyl macrogol-32 glycerides EP Lauroyl polyoxyl-32 glycerides NF Lauroyl polyoxylglycerides (USA FDA IIG)), NF | | 1.500 | 3.00 | 30.00 |
| | Total: | | 100.000 | 200.00 mg | 2000.00 |

The manufacturing process is as follows. CAPMUL MCM (Medium Chain Mono- and Diglycerides) is heated to 65° C.

GELUCIRE 44/14 (Lauroyl macrogol-32 glycerides EP Lauroyl polyoxyl-32 glycerides NF Lauroyl polyoxylglycerides (USA FDA IIG)) is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 14

In an exemplary embodiment, a capsule is provided containing a fill material having fully solubilized estradiol and partially solubilized progesterone comprising:

TABLE 17

| Item No. | Ingredient(s) | Label Claim (mg) | % w/w | Qty/ Capsule (mg) | Amount/ Batch (g) |
|---|---|---|---|---|---|
| 1. | Progesterone, USP, micronized | 200.00 | 33.33 | 200.0 | 2000.0 |
| 2. | Estradiol Hemihydrate | 2.00 | 0.35 | 2.07 | 20.7 |
| 3. | CAPMUL MCM (Medium Chain Mono- and Diglycerides), NF | | 65.32 | 391.93 | 3919.3 |
| 4. | GELUCIRE 44/14 (Lauroyl macrogol-32 glycerides EP Lauroyl polyoxyl-32 glycerides NF Lauroyl polyoxylglycerides (USA FDA IIG)), NF | | 1.00 | 6.0 | 60.0 |
| | Total: | | 100.00 | 600.0 mg | 6000.0 |

The manufacturing process is as follows. CAPMUL MCM (Medium Chain Mono- and Diglycerides) is heated to 65° C. Gelucire 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 15

Progesterone and Estradiol Combination Study under Fed Conditions.

This following study protocol was used to establish bio-availability and bio-equivalence parameters for a combination product of the present disclosure comprising progesterone (200 mg) and estradiol (2.0 mg) as prepared via the process described in Example 14 and compared to 200 mg of PROMETRIUM (progesterone, USP) (Catalent Pharmaceuticals, St. Petersburg, Fla. (and 2.0 mg of ESTRACE (estradiol vaginal cream, USP, 0.01%) (Bristol-Myers Squibb Co. Princeton, N.J.), administered to twenty-four (24) normal healthy, adult human post-menopausal female subjects under fed conditions.

The Study Design: An open-label, balanced, randomized, two-treatment, two-period, two-sequence, single-dose, two-way crossover.

The subjects were housed in the clinical facility from at least 11.00 hours pre-dose to at least 48.00 hours post-dose in each period, with a washout period of at least 14 days between the successive dosing days.

Subjects were fasted for at least about 10.00 hours before being served a high-fat, high-calorie breakfast, followed by dosing, then followed by a 04.00 hour, post-dose additional period of fasting.

Standard meals were provided at about 04.00, 09.00, 13.00, 25.00, 29.00, 34.00 and 38.00 hours post-dose, respectively.

Water was restricted at least about 01 hour prior to dosing until about 01 hour post-dose (except for water given during dosing). At other times, drinking water was provided ad libitum.

Subjects were instructed to abstain from consuming caffeine and/or xanthine containing products (i.e. coffee, tea, chocolate, and caffeine-containing sodas, colas, etc.) for at least about 24.00 hours prior to dosing and throughout the study, grapefruit and\or its juice and poppy containing foods for at least about 48.00 hours prior to dosing and throughout the study.

Subjects remained seated upright for about the first 04.00 hours post-dose and only necessary movements were allowed during this period. Thereafter subjects were allowed to ambulate freely during the remaining part of the study. Subjects were not allowed to lie down (except as directed by the physician secondary to adverse events) during restriction period.

Subjects were instructed not to take any prescription medications within 14 days prior to study check in and throughout the study. Subjects were instructed not to take any over the counter medicinal products, herbal medications, etc. within 7 days prior to study check-in and throughout the study.

After overnight fasting of at least about 10.00 hours, a high-fat high-calorie breakfast was served about 30 minutes prior to administration of investigational product(s). All subjects were required to consume their entire breakfast within about 30 minutes of it being served, a single dose of either test product (T) of Progesterone 200 mg & Estradiol 2 mg tablets or the reference product (R) PROMETRIUM (progesterone, USP) soft gel Capsule 200 mg and ESTRACE (estradiol vaginal cream, USP, 0.01%) (Estradiol) Tablets 2 mg (according to the randomization schedule) were administered with about 240 mL of water under fed condition, at ambient temperature in each period in sitting posture. A thorough mouth check was done to assess the compliance to dosing.

All dosed study subjects were assessed for laboratory tests at the end of the study or as applicable.

In each period, twenty-three (23) blood samples were collected. The pre-dose (10 mL) blood samples at −01.00, −00.50, 00.00 hours and the post-dose blood samples (08 mL each) were collected at 00.25, 00.50, 00.67, 00.83, 01.00, 01.33, 01.67, 02.00, 02.50, 03.00, 04.00, 05.00, 06.00, 07.00, 08.00, 10.00, 12.00, 18.00, 24.00 and 48.00 hours in labeled K2EDTA—vacutainers via an indwelling cannula placed in one of the forearm veins of the subjects. Each intravenous indwelling cannula was kept in situ as long as possible by injecting about 0.5 mL of 10 IU/mL of heparin in normal saline solution to maintain the cannula for collection of the post-dose samples. In such cases blood samples were collected after discarding the first 0.5 mL of heparin containing blood. Each cannula was removed after the 24.00 hour sample was drawn or earlier or if blocked.

At the end of the study, the samples were transferred to the bio-analytical facility in a box containing sufficient dry ice to maintain the integrity of the samples. These samples were stored at a temperature of −70° C.±20° C. in the bio-analytical facility until analysis.

Progesterone (Corrected and Uncorrected) and Estradiol (unconjugated) and estrone (total) in plasma samples is assayed using a validated LC-MS/MS method.

Fasted studies using this protocol were also conducted. However, rather than the high-fat meal prior to administration of the test and reference drug, each subject fasted for a period of at least twelve (12) hours prior to dose administration.

Example 16

Figure 2:
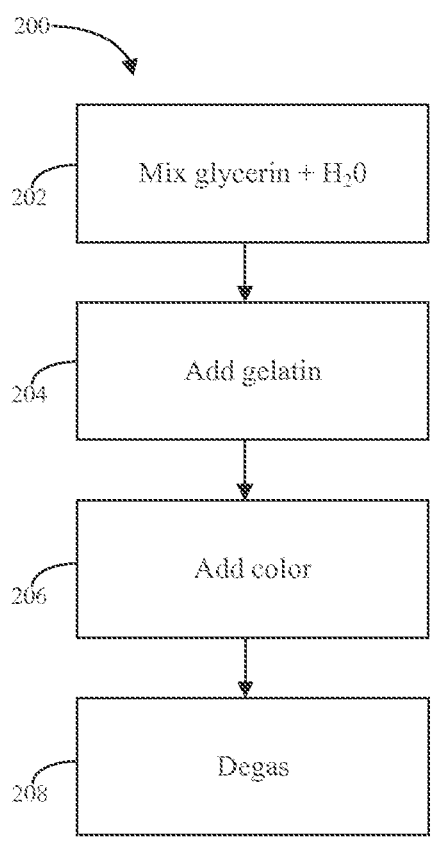
FIG. 2 illustrates an exemplary manufacturing process of a softgel material in accordance with various embodiments.
Figure 3:
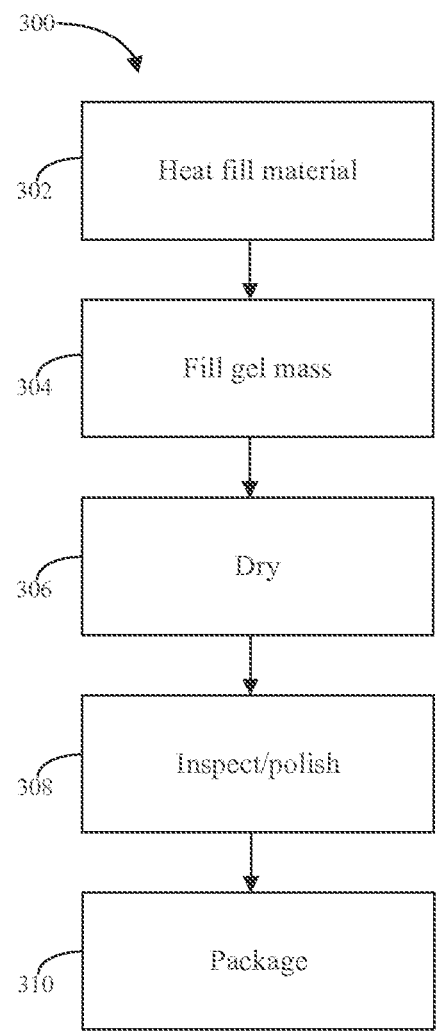
FIG. 3 illustrates an exemplary manufacturing process in accordance with various embodiments.

Method of manufacture in accordance with various embodiments are shown in FIGS. 1-3. With reference to FIG. 1, method of fill material 100 is shown. Step 102 comprises heating an oily vehicle carrier to 40° C.±5° C. Heating may be accomplished through any suitable means. The heating may be performed in any suitable vessel, such as a stainless steel vessel. The oily vehicle may be any oily vehicle described herein, for example, CAPMUL MCM (Medium Chain Mono- and Diglycerides).

Step 104 comprises mixing Gelucire 44/14 with the oily vehicle. Mixing may be facilitated by an impellor, agitator, or other suitable means. Step 102 may be performed under an inert or relatively inert gas atmosphere, such as nitrogen gas $N_2$. Mixing may be performed in any suitable vessel, such as a stainless steel vessel.

Step 106 comprises mixing estradiol into the mixture of the oily vehicle and Gelucire 44/14. Mixing may occur in a steel tank or vat. Mixing may be facilitated by an impellor, agitator, or other suitable means. Step 106 may be performed under an inert or relatively inert gas atmosphere, such as nitrogen gas $N_2$.

Step 108 comprises cooling to room temperature. Cooling may be allowed to occur without intervention or cooling may be aided by application of a cooling system.

Step 110 comprises mixing micronized progesterone into the mixture of oily vehicle, estradiol and Gelucire 44/14. Mixing may occur in a steel tank or vat. Mixing may be facilitated by an impellor, agitator, or other suitable means. Step 110 may be performed under an inert or relatively inert gas atmosphere, such as nitrogen gas $N_2$. Step 112 comprises degasing. The resulting mixture from step 112 may comprise a fill material suitable for production into a softgel capsule.

With reference to FIG. 2, softgel capsule, i.e. gel mass, production 200 is shown. Step 202 comprises mixing glycerin with water. The water used in step 202 may be purified by any suitable means, such as reverse osmosis, ozonation, filtration (e.g., through a carbon column) or the like. Mixing may be facilitated by an impellor, agitator, or other suitable means. Step 202 may be performed under an inert or relatively inert gas atmosphere, such as nitrogen gas $N_2$. Heating may be performed until the temperature reaches 80° C.±5° C.

Step 204 comprises the addition of gelatin to the glycerin water mixture. Mixing may be facilitated by an impellor, agitator, or other suitable means. Step 204 may be performed under an inert or relatively inert gas atmosphere, such as nitrogen gas $N_2$. A vacuum may be drawn in step 204 to de-aerate.

Step 206 comprises addition of a coloring agent such as a dye. A coloring agent may comprise products sold under the trademark OPATINT or other suitable agent. Step 206 may be performed under an inert or relatively inert gas atmosphere, such as nitrogen gas $N_2$. Step 208 comprises degasing. The resulting mixture from step 208 may comprise a gel capsule material suitable for use as a gel capsule in production of a softgel capsule.

With reference to FIG. 3, softgel capsule assembly process 300 is shown. Step 302 comprises heating the fill material. The fill material may be heated to any suitable temperature. In various embodiments, the fill material is heated to 30° C.+/−3° C. Fill material may be heated in a fill hopper. A fill hopper may comprise a device configured to hold a volume of the fill material and/or to dispense the fill material in controlled volumes. Step 304 comprises filling a gel mass. A gel mass may be taken from the gel capsule material produced in step 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812 (Caprylic/Capric Triglyceride) or other suitable lubricant. Step 304 thus produces one or more softgel capsules. Filling may comprise producing a ribbon of thickness 0.85 mm±0.05 mm using spreader box knobs. The fill material may be injected into the gel to produce a fill weight having target weight±5% (i.e., 650±33 mg and 325±16.3 mg).

Step 304 comprises filling a gel mass. A gel mass may be taken from the gel capsule material produced in step 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812 or other suitable lubricant. Step 304 thus produces one or more softgel capsules. Filling may comprise producing a ribbon of thickness 0.85 mm±0.05 mm using spreader box knobs. The fill material may be injected into the gel to produce a fill weight having target weight±5% (i.e., 650±33 mg and 325±16.3 mg).

Step 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Step 308 may comprise inspection and/or polishing. Polishing may be performed with isopropyl alcohol. Step 310 may comprise packaging. Packaging may be accomplished through any suitable means. Packaging may comprise packing softgel capsules into a blister pack, bottle, box, pouch, or other acceptable packaging.

We claim:

1. A method of treating a menopause-related symptom in a woman comprising:
    administering to the woman an effective amount of a pharmaceutical composition, the pharmaceutical composition comprising solubilized estradiol, suspended progesterone, and a solubilizing agent;
    wherein each of the estradiol and the suspended progesterone are present in the solubilizing agent and the estradiol and the suspended progesterone are uniformly dispersed;
    wherein the solubilizing agent contains an effective amount of C6-C12 oil; and
    wherein at least about 90% of the estradiol is solubilized in the solubilizing agent.

2. The method of claim 1, further comprising partially solubilized progesterone, the partially solubilized progesterone being solubilized in the solubilizing agent.

3. The method of claim 1, wherein the composition is formulated as a gelatin capsule.

4. The method of claim 1, wherein the C6-C12 oil is selected from at least one of mono-, di-, and triglycerides and combinations thereof.

5. The method of claim 1, wherein the estradiol has a dosage strength of at least about 0.125 mg and wherein the progesterone has a dosage strength of at least about 25 mg.

6. The method of claim 1, wherein the ratio of progesterone to estradiol is about 24:1, about 25:1, about 96:1, about 100:1, about 192:1, or about 200:1.

7. The method of claim 1, wherein the composition is bioequivalent to a 200 mg progesterone soft gel capsule and to a 2 mg estradiol tablet.

8. A method of treating a menopause symptom in a woman comprising administering a pharmaceutical composition to the woman, the pharmaceutical composition comprising:
   solubilized estradiol;
   suspended progesterone; and
   a solubilizing agent, the solubilizing agent containing an effective amount of a C6-C12 oil;
   wherein the estradiol and the suspended progesterone are present in the solubilizing agent, the estradiol and the suspended progesterone are uniformly dispersed and at least about 90% of the estradiol is solubilized in the solubilizing agent; and
   wherein the estradiol does not precipitate for at least 14 days.

9. The method of claim 8, further comprising partially solubilized progesterone, the partially solubilized progesterone being solubilized in the solubilizing agent.

10. The method of claim 8, wherein the composition is formulated as a gelatin capsule.

11. The method of claim 8, wherein the C6-C12 oil is selected from at least one of mono-, di-, and triglycerides and combinations thereof.

12. The method of claim 8, wherein the estradiol has a dosage strength of at least about 0.125 mg and wherein the progesterone has a dosage strength of at least about 25 mg.

13. The method of claim 8, wherein the ratio of progesterone to estradiol is about 24:1, about 25:1, about 96:1, about 100:1, about 192:1, or about 200:1.

14. The method of claim 8, wherein the composition is bioequivalent to a 200 mg progesterone soft gel capsule and to a 2 mg estradiol tablet.

15. A method of treating a menopause symptom comprising:
   administering an effective amount of a pharmaceutical composition to a woman, the pharmaceutical composition comprising solubilized estradiol, suspended progesterone, and a solubilizing agent, the estradiol being stable in the solubilizing agent for at least 14 days;
   wherein each of the estradiol and the suspended progesterone are present in the solubilizing agent and the estradiol and the suspended progesterone are uniformly dispersed;
   wherein at least about 90% of the estradiol is solubilized in the solubilizing agnent, and wherein the solubilizing agent contains an effective amount of a C6-C12 oil.

16. The method of claim 15, further comprising partially solubilized progesterone, the partially solubilized progesterone being solubilized in the solubilizing agent.

17. The method of claim 15, wherein the composition is formulated as a gelatin capsule.

18. The method of claim 15, wherein the C6-C12 oil is selected from at least one of mono-, di-, and triglycerides and combinations thereof.

19. The method of claim 15, wherein the estradiol has a dosage strength of at least about 0.125 mg and wherein the progesterone has a dosage strength of at least about 25 mg.

20. The method of claim 15, wherein the ratio of progesterone to estradiol is about 24:1, about 25:1, about 96:1, about 100:1, about 192:1, or about 200:1.

* * * * *

UNITED STATES PATENT AND TRADEMARK OFFICE
CERTIFICATE OF CORRECTION

PATENT NO. : 8,846,648 B2  
APPLICATION NO. : 14/099545  
DATED : September 30, 2014  
INVENTOR(S) : Brian A. Bernick et al.

Page 1 of 1

It is certified that error appears in the above-identified patent and that said Letters Patent is hereby corrected as shown below:

On the Title Page

At item (72), please add inventor --Frederick D. Sancilio, Palm Beach Gardens, FL (US)--

Signed and Sealed this  
Twenty-sixth Day of March, 2019

Andrei Iancu  
*Director of the United States Patent and Trademark Office*

UNITED STATES PATENT AND TRADEMARK OFFICE
CERTIFICATE OF CORRECTION

PATENT NO. : 8,846,648 B2  
APPLICATION NO. : 14/099545  
DATED : September 30, 2014  
INVENTOR(S) : Brian A. Bernick et al.

It is certified that error appears in the above-identified patent and that said Letters Patent is hereby corrected as shown below:

In the Claims

Column 24, Claim 15, Line 16: Delete "agnent" and insert in its place --agent--.

Signed and Sealed this
Twentieth Day of August, 2019

Andrei Iancu
*Director of the United States Patent and Trademark Office*